(12) United States Patent
Kim et al.

(10) Patent No.: US 9,417,216 B2
(45) Date of Patent: Aug. 16, 2016

(54) ATOMIC LAYER DEPOSITION INVERTED PASSIVATED SURFACE ACOUSTIC WAVE SENSOR FOR EARLY DETECTION OF BIOFILM GROWTH

(71) Applicant: University of Maryland, College Park, MD (US)

(72) Inventors: Young Wook Kim, Seoul (KR); Reza Ghodssi, Potomac, MD (US); Agisilaos A. Iliadis, Edgewater, MD (US); William E. Bentley, Annapolis, MD (US); Mariana Tsacoumis Meyer, Baltimore, MD (US)

(73) Assignee: University of Maryland, College Park, MD (US)

( * ) Notice: Subject to any disclaimer, the term of this patent is extended or adjusted under 35 U.S.C. 154(b) by 31 days.

(21) Appl. No.: 14/157,094

(22) Filed: Jan. 16, 2014

(65) Prior Publication Data

US 2014/0199757 A1 Jul. 17, 2014

Related U.S. Application Data

(60) Provisional application No. 61/753,332, filed on Jan. 16, 2013.

(51) Int. Cl.
*C12M 1/34* (2006.01)
*G01N 29/28* (2006.01)
*G01N 29/02* (2006.01)
*G01N 29/036* (2006.01)

(52) U.S. Cl.
CPC ............. *G01N 29/28* (2013.01); *G01N 29/022* (2013.01); *G01N 29/036* (2013.01); *G01N 2291/0256* (2013.01); *G01N 2291/0258* (2013.01); *G01N 2291/0423* (2013.01)

(58) Field of Classification Search
CPC ............. G01N 2291/0256; G01N 2291/0423; G01N 29/022; G01N 2291/0255; G01N 29/036; G01N 29/2437; G01N 29/28; G01N 33/54373; B01L 2400/0436; B01L 3/502707; B01L 3/50273
See application file for complete search history.

(56) References Cited

PUBLICATIONS

Kim et al.,"A Bacterial Biofilm Surface Acoustic Wave Sensor for Real Time Biofilm Growth Monitoring", IEEE Sensors Nov. 1-4, 2010 Conference, pp. 1568-1571.*
Kim et al.,"An ALD aluminum oxide passivated Surface Acoustic Wave sensor for early biofilm detection" Sensors and Actuators B 163 (published online Jan. 16, 2012) 136-145.*

(Continued)

*Primary Examiner* — Dennis M White
(74) *Attorney, Agent, or Firm* — Carter, DeLuca, Farrell & Schmidt, LLP

(57) ABSTRACT

A surface acoustic wave (SAW) biofilm sensor includes a transmitting electric to acoustic wave transducer defining an upper surface and a lower surface, a receiving acoustic wave to electric transducer defining an upper surface and a lower surface, a piezoelectric film layer defining an upper surface and a lower surface, and a passivation film layer defining an upper surface and a lower surface. Portions of the lower surface of the piezoelectric film layer are disposed on the upper surface of the transmitting electric to acoustic wave transducer and on the upper surface of the receiving acoustic wave to electric transducer, and the lower surface of the passivation film layer is disposed on the upper surface of the piezoelectric film layer such that the upper surface of the passivation film layer is configured to enable contact with a biofilm.

39 Claims, 26 Drawing Sheets

(56) References Cited

PUBLICATIONS

Kim, "An atomic layer deposition passivated Surface Acoustic Wave sensor for bacterial biofilm growth monitoring", Dissertation, University of Maryland, College Park, First publically available Apr. 4, 2013.*
J. W. Costerton et al., Bacterial Biofilms: A Common Cause of Persistent Infections, Science, vol. 284, (1999), p. 1318-1322.
Sutherland, I. W., Bacterial exopolysaccharides—their nature and production, Surface Carbohydrates of the Prokaryotic Cell, London, Academic Press, (1977), p. 27-96.
J. W. Costerton, et al., Bacterial Biofilms in Nature and Disease, Annu. Rev. Microbiol, 41, (1987), p. 435-506.
Liju Yang, et al., Detection of viable *Salmonella* using microelectrode-based capacitance measurement coupled with immunomagnetic separation, Journal of Microbiological Methods, 64, (2006), p. 9-16.
Ebrahim Ghafar-Zadeh, et al., Bacteria Growth Monitoring Through a Differential CMOS Capacitive Sensor, IEEE Transactions on Biomedical Circuits and Systems, vol. 4, No. 4, (2010), p. 232-238.
X. Munoz-Berbel, et al., Impedimetric approach for quantifying low bacteria concentrations based on the changes produced in the electrode-solution interface during the pre-attachment stage, Biosensors and Bioelectronics., 23, (2008), p. 1540-1546.
E. Spiller, et al., A sensitive microsystem as biosensor for cell growth monitoring and antibiotic testing, Sensors and Actuators A, 130-131, (2006), p. 312-321.
Ewa Heyduk, et al., Fluorescent homogeneous immunosensors for detecting pathogenic bacteria, Analytical Biochemistry, (2010), p. 396, 298-303.
Benjamin J. Privett, et al., Electrochemical Sensors, Anal. Chem., (2010), 82, p. 4723-4741.
Michiel van Leeuwen, et al., Aerobic Batch Cultivation in Micro Bioreactor with Integrated Electrochemical Sensor Array, Biotechnol. Prog., vol. 26, No. 1, (2010), p. 293-300.
G. L. Harding, et al., Love wave acoustic immunosensor operating in liquid, Sensors and Actuators A, 61, (1997), p. 279-286.
J. Du, et al., A study of Love-wave acoustic sensors, Sensors and Actuators A, 56, (1996), p. 211-219.
J. Du, et al., An experimental study of Love-wave acoustic sensors operating in liquids, Sensors and Actuators A, 60, (1997), p. 54-61.
K. Z. Kourosh, et al., Novel Love mode surface acoustic wave based immunosensors, Sensor and Actuators B, 91, (2003), p. 143-147.
S. Krishnamoorthy, et al., Properties of high sensitivity ZnO surface acoustic wave sensors on SiO2/(100) Si substrates, Solid-State Electronics, 52, (2008), p. 1710-1716.
H. Morkoc, et al., Zinc Oxide: Fundamentals, Materials and Device Technology (Chapter 1: General Properties of ZnO), Wiley-VCH Verag GmbH, Weinheim, 2009.
R. D. Vispute et al., High quality crystalline ZnO buffer layers on sapphire (001) by pulsed laser deposition for III-V nitrides, Applied Physics Letters 70 2735 (1997), p. 2735-2737.
S. Krishnamoorthy, et al., Development of high frequency ZnO/SiO2/Si Love mode surface acoustic wave devices, Solid-State Electronics, 50, (2006), p. 1113-1118.
S. Krishnamoorthy, et al., An interleukin-6 ZnO/SiO2/Si surface acoustic wave biosensor, Biosensors and Bioelectronics, 24, (2008), p. 313-318.
M. C. Horrillo et al., Optimization of SAW sensors with a structure ZnO—SiO2—Si to detect volatile organic compounds, Sensors and Actuators B, 118, (2006), p. 356-361.
X. Chen, D. Liu, Temperature stability of ZnO-based Love wave biosensor with SiO2 buffer layer, Sens. Actuat. A, 156, (2009), p. 317-322.
X. Chen, D. Liu, J. Chen, G. Wang, The effect of a SiO2 layer on the performance of a ZnO-based SAW device for high sensitivity biosensor applications, Smart Mater. Struct. 18, (2009), 115021 (8 pp).
A. Springer, R. Weigel, A. Pohl, F. Seifert, Wireless identification and sensing using surface acoustic wave devices, IEEE ASME Trans Mechatron, 9,(1999), p. 745-756.
Alfred Pohl, A Review of Wireless SAW Sensors, IEEE Transactions on Ultrasonics, Ferroelectrics and Frequency Control, vol. 47, No. 2, (Mar. 2000), p. 317-332.
Arruda David L, Wilson William C, Nguyen Crystal, Yao Qi W, Caiazzo Robert, Talpasanu Ilie, Dow Douglas, Liu Brian, Microelectrical sensors as emerging platforms for protein biomaker detection in point-of-care diagnostics, Expert Rev. Mol. Diagn., vol. 9, No. 7, (2009), p. 749-755.
M. Bisoffi, B. Hjelle, D.C. Brown, D.W. Branch, T.L. Edwards, S.M. Brozik, V.S. Bondu-Hawkins, R. S. Larson, Detection of viral bioagents using a shear horizontal surface acoustic wave biosensor, Biosensors & Bioelectronics, 23, (2008), pp. 1397-1403.
Y.Q.Fu, J.K. Luo, X.Y. Du, A.J. Flewitt, Y. Li, G.H. Markx, A.J. Walton, W.I. Milne, Recent developments on ZnO films for acoustic wave bio-sensing and microfluidic applications: a review, Sensors and Actuators B-CHEM, 143, (2010), p. 606-619.
Irie RF, Natural antibody in human serum to neoantigen in human cultured cells grown in fetal bovine serum, J. Natl Cancer Inst, 52(4), (1974), p. 1051-1058.
Glen McHale, Generalized concept of shear horizontal acoustic plate mode and Love wave sensors, Institute of physics publishing, Meas. Sci Technol. 14, (2003), p. 1847-1853.
Biljana A. Cavic, Gordon L. Hayward, and Michael Thompson, Acoustic waves and the study of biochemical macromolecules and cells at the sensor-liquid interface, The Analyst, 124, (1999), p. 1405-1420.
Bill Drafts, Acoustic Wave Technology Sensors, IEEE Transactions on Microwave Theory and Techniques, vol. 49, No. 4, (2001), p. 795-802.
Federal Communications Commission, Title 47 C.F.R., Chapter I, Subchapter D, Part 95, Subpart I, paragraph 1209, "Permissible communications", 77 FR 55733, as amended through Sep. 11, 2012.
Douglas H. Lowndes, D.B. Geohegan, A.A. Puretzky, D.P. Norton, C. M. Rouleau, Synthesis of Novel Thin-Film Materials by Pulsed Laser Deposition, Science, vol. 273, (1996), p. 898-903.
Susan E. Voss and Jont B. Allen, Measurement of acoustic impedance and reflectance in the human ear canal, J. Acoust. Soc. Am, 95 (1), (1994), p. 372-384.
B. Jakoby, M.J. Vellekoop, Properties of Love waves: applications in sensors, Smart Mater. Struct. 6, (1997), p. 668-679.
J. Su, Z. B. Kuang, H. Liu, Love wave in ZnO/SiO2/Si structure with initial stresses, Journal of Sound and Vibration, 286, (2005), p. 981-999.
R. C. Chang, S. Y. Chu, C. S. Hong, Y. T. Chuang, A study of Love wave devices in ZnO/Quartz and ZnO/LitaO3 structures, Thin Soild Films, 498, (2006), 146-151.
W. C. Shih, H. Y. Su, M. S. Wu, Deposition of ZnO thin films on SiO2/Si substrate with Al2O3 buffer layer by radio frequency magnetron sputtering for high frequency surface acoustic wave devices, Thin Solid Films, 517, (2009), p. 3378-3381.
W. C. Shih, T. L. Wang, L. L. Hsu, Surface acoustic wave properties of aluminum oxide films on lithium niobate, Thin Soild Films, 518, (2010), p. 7143-7146.
J. Du, G. L. Harding, A multilayer structure for Love-mode acoustic sensors, Sensors and Actuator A, 65, (1998), p. 152-159.
NIST Property Data Summaries, http://www.ceramics.nist.gov/srd/summary/emodox00.htm.
Lenntech B.V., http://www.lenntech.com/teflon.htm, c. 1998-2014.
Hang-Ju Ko, Myung-Soo Han, Young-Sik Park, Yun-Sik Yu, Byoung-In Kim, Sang Sub Kim, Jin-Hyeok Kim, Improvement of the quality of ZnO substrates by annealing, Journal of Crystal Growth, 269, (2004), p. 493-498.
Siu, Louis "Mass of a Bacterium", The Physics Factbook, Elert, Glenn ed., pp. 1-2, http://hypertextbook.com/facts/2003/LouisSiu.shtml, 2003.
Jeffrey V. Straight and Doraiswami Ramkrishna, Modeling of Bacterial Growth under Multiply-Limiting Conditions. Experiments under Carbon- or/and Nitrogen-Limiting Conditions, Biotechnol. Prog. 10, (1994), p. 588-605.
Augustin J.C et al., Significance of Inoculum Size in the Lag Time of Listeria monocytogenes, Appl. Envion. Microbiol. vol. 66, (2000), p. 1706-1710.

(56) References Cited

OTHER PUBLICATIONS

Mariana T Meyer, Varnika Roy, William E Bentley, and Reza Ghodssi, Development and validation of a microfluidic reactor for biofilm monitoring via optical methods, J. Micromech. Microeng., 21, (2011), 054023 (10 pp).

Federal Communications Commission, Title 47 C.F.R., Chapter I, Subchapter D, Part 95, Subpart E, paragraph 627, "MedRadio transmitters in the 401-406 MHz band", as amended through 77 FR 4268, Jan. 27, 2012.

Federal Communications Commission, Title 47 C.F.R., Chapter I, Subchapter D, Part 95, Subpart I, paragraph 1209, "Permissible communications", 79 FR 60100, as amended through Oct. 6, 2014.

Sutherland. Bacterial exopolysaccharides—their nature and production. Antibiotics and chemotherapy 1989; 42:50-55.

* cited by examiner

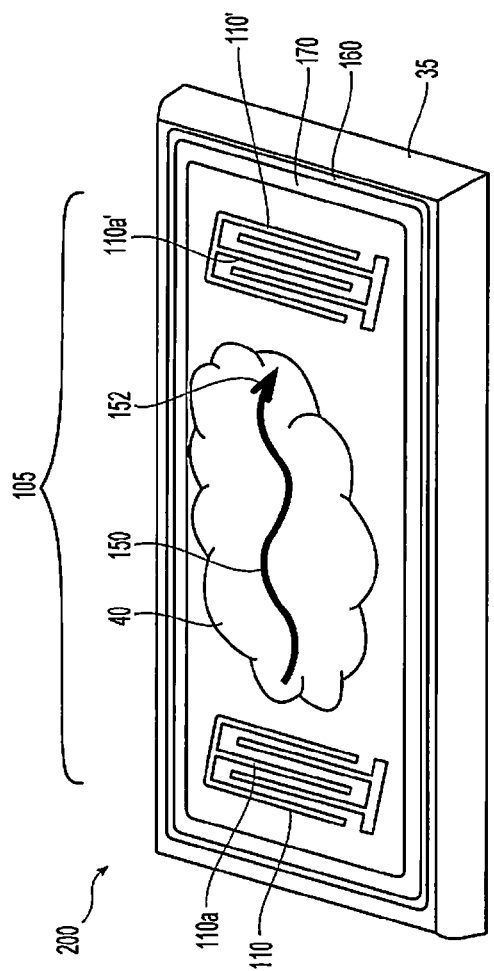
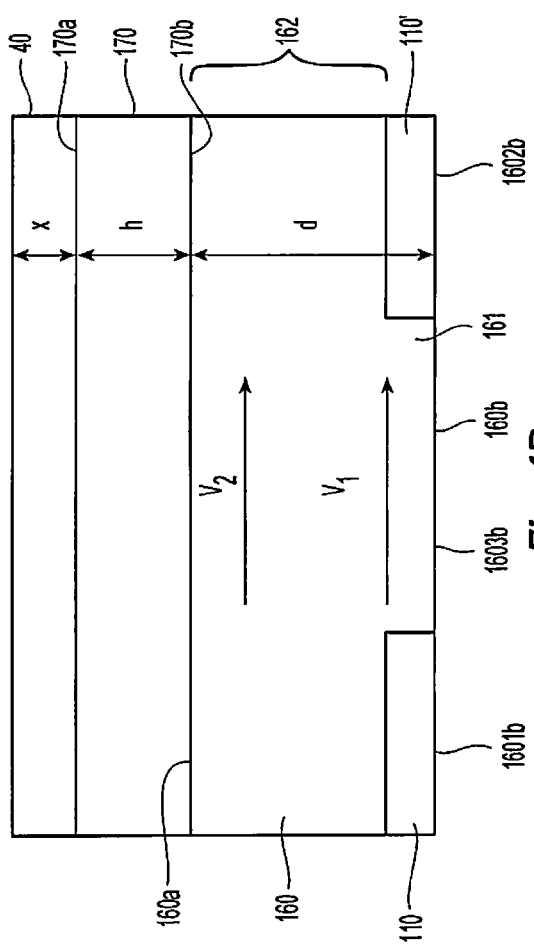

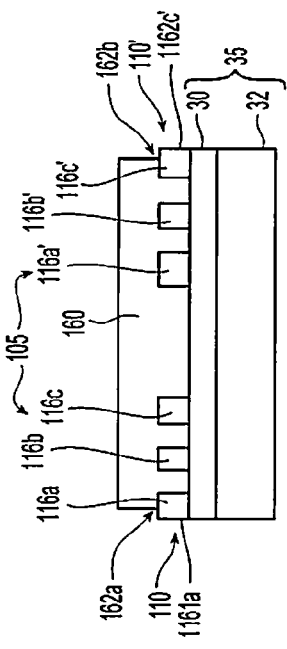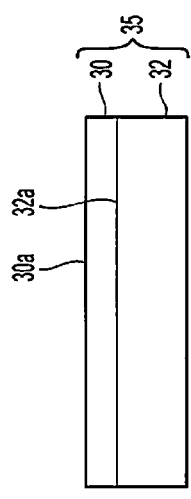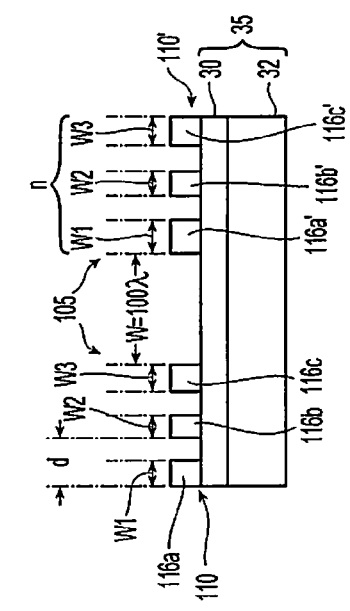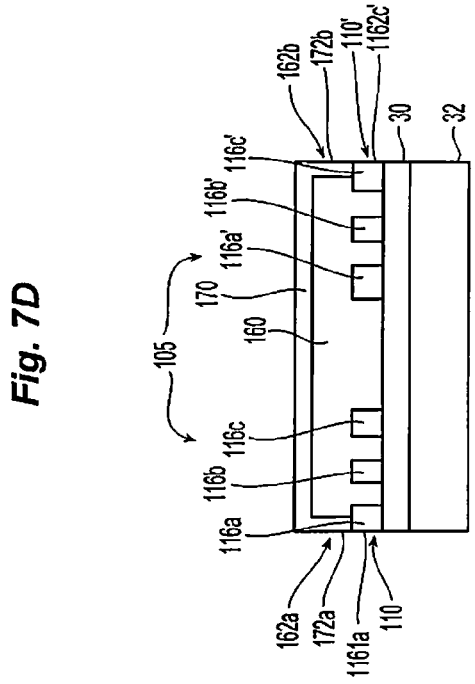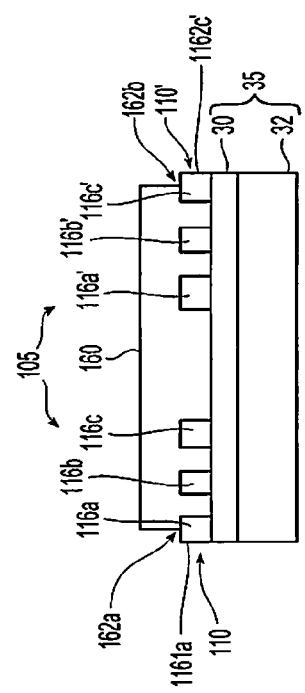

After ultrasonication cleaning in acetone for 3 hours

After DI water cleaning

After 2nd biofilm growth experiment and oxygen plasma cleaning

After oxygen plasma cleaning for 30s

ATOMIC LAYER DEPOSITION INVERTED PASSIVATED SURFACE ACOUSTIC WAVE SENSOR FOR EARLY DETECTION OF BIOFILM GROWTH

CROSS-REFERENCE TO RELATED APPLICATIONS

This application claims the benefit of, and priority to, U.S. Provisional Patent Application Ser. No. 61/753,332, filed on Jan. 16, 2013, entitled "ALD Passivated Bacterial Biofilm Sensor Using Inverted Surface. Acoustic Wave" by Young Wook Kim et al., the entire contents of which is hereby incorporated by reference herein.

STATEMENT OF GOVERNMENT SUPPORT

This invention was made with U.S. government support under EFRI1042881 awarded by the National Science Foundation. The U.S. government has certain rights in the invention.

BACKGROUND

1. Technical Field

The present disclosure relates to surface acoustic wave (SAW) sensors for detecting the growth of biofilms. More particularly, the present disclosure relates to piezoelectric SAW sensors having passivation film layer.

2. Background of Related Art

Bacteria can attach to surfaces and form microcolonies as their population increases. The colonies eventually can form a community known as a bacterial biofilm [1, 2]. A biofilm is not simply a group of bacteria, but a complex collection of microorganisms encased in an extracellular matrix. The extracellular matrix is composed of exopolysaccharide polymers which promote irreversible adhesion of microcolonies on the surface and also prevent diffusion of antibiotics through the biofilm [1, 2]. Due to the complex extracellular matrix and heterogeneous bacterial composition, biofilms are resistant to bacteriophages in industry and to chemically diverse antibiotic treatments in clinical fields [3]. In addition, bacterial corrosion of metals is an economically important consequence of bacterial biofilm formation that illustrates several fascinating aspects of the structure and physiology of these adherent bacterial populations. Therefore, environmental, clinical, and industrial long term reliable biofilm growth monitoring is critical to prevent contamination, severe infection, and corrosive problems due to the biofilm formation.

The measurement of bacterial biofilms with capacitive sensing has been applied by Yang and Li to monitor *Salmonella typhimurium* bacteria [4], and by Ghafar-Zadeh et al. to detect *Escherichia coil (E. coli)* [5]. In Yang and Li at al. [4], an interdigitated microelectrode was fabricated to provide detectable impedance signals in capacitance measurement during bacterial growth, *S. typhimurium* bacteria were grown over the microelectrode and the capacitance change was continuously measured. Capacitive sensing in a liquid environment, however, can be interfered with by a conductive media due to the current flow through the growth media [4].

The direct impedance measurement of the attachment of *E. coli* on an electrode is demonstrated by other groups [6, 7]. The change of impedance during bacterial growth is correlated with the biomass adhere on the electrode. This impedimetric sensing is particularly useful in detecting very early attachment of bacteria based on the significant impedance change observed upon attachment. However, long-term real-time biofilm monitoring by impedance measurement requires a continuous current source for bacterial detection which may cause interruption of bacterial growth.

Fluorescent methods have reported high sensitivity [8], but require fluorescent molecule labeling for sensing to occur. Labeling requires additional sample preparation and the fluorescent molecule can be degraded over long term exposure to liquid.

Electrochemical sensing can be used for selective detection a molecule without fluorescent labeling [9]. An electrochemical sensor array was integrated with a miniaturized bioreactor system for high throughput cell cultivation in 96 well plates [10]. Using a 100 μl working volume in the 96 well micro reactors, the sensor array can monitor temperature, pH, and oxygen concentration as well as total biomass. However, electrochemical sensors require a continuous power source for the operation and also require recalibration of the sensor due to the conductivity change of bacterial growth media in long term biofilm growth experiments.

Surface Acoustic Wave (SAW) sensors exhibit several advantages in small molecule detection including high sensitivity [11-22] and low power consumption [23]. A SAW sensor can detect mass or viscosity change due to the wave velocity attenuation, resulting in a resonant frequency shift at the output. A highly sensitive SAW sensor for detection of interleukin-6 (IL-6), which is one of key molecules in human immune system, was reported. In Krishnamoorthy et al. [19], a specific receptor for IL-6 was immobilized on the surface of the SAW sensor. Based on the resonant frequency shift due to the IL-6 binding, the detection limit of the SAW sensor was approximately $10^{-18}$ g (grams). A SAW sensor is also a passive device.

The power for operation of the SAW sensor can be delivered by an external device wirelessly which makes the SAW sensor useful for long term biofilm monitoring without a continuous power supply [23]. Furthermore, the SAW sensor can be fabricated using biocompatible materials [24-26]. The combination of extremely high sensitivity, biocompatibility, and low power consumption makes the SAW sensor a unique tool for real time monitoring of bacterial biofilm growth. However, it is also noted that piezoelectric materials used in the SAW sensor can be dissolved due to long term exposure to liquid [27].

SUMMARY

The present disclosure relates to a novel inverted passivated SAW sensor for real time biofilm monitoring. A piezoelectric film is deposited by pulsed laser deposition, and the sensor is effectively passivated by a passivated film layer using atomic layer deposition to prevent damage to the piezoelectric layer in bacterial growth media and animal serum.

The SAW sensor can be reused after oxygen plasma cleaning, allowing for consecutive biofilm formation experiments using one sensor.

Therefore, the present disclosure relates to a novel surface acoustic wave (SAW) biofilm sensor comprising: a SAW transducer; a piezoelectric film layer; and a passivation film layer. The piezoelectric film layer is mounted over the SAW transducer and the passivation film layer is mounted over the piezoelectric film layer. In one embodiment, the passivation layer includes aluminum oxide, $Al_2O_3$. In yet another embodiment, the passivation layer defines a thickness of at least 45 nanometers (nm). In a still further embodiment, the piezoelectric layer includes zinc oxide, ZnO. In yet another embodiment, the piezoelectric layer defines a thickness of at least 40 nanometers (nm).

The present disclosure relates also to a surface acoustic wave (SAW) biofilm sensor that includes a transmitting electric to acoustic wave transducer defining an upper surface and a lower surface, a receiving acoustic wave to electric transducer defining an upper surface and a lower surface, a piezoelectric film layer defining an upper surface and a lower surface and a passivation film layer defining an upper surface and a lower surface. A portion of the lower surface of the piezoelectric film layer is disposed on the upper surface of the transmitting electric to acoustic wave transducer and another portion of the lower surface of the piezoelectric film layer is disposed on the upper surface of the receiving acoustic wave to electric transducer and the lower surface of the passivation film layer is disposed on the upper surface of the piezoelectric film layer. The upper surface of the passivation film layer thereby configured to enable contact with a biofilm.

In one embodiment, the SAW biofilm sensor may further include a piezoelectric SAW loss reduction film layer defining an upper surface and a lower surface wherein the lower surface of the transmitting electric to acoustic wave transducer is disposed on a portion of the upper surface of the piezoelectric SAW loss reduction film layer and wherein the lower surface of the receiving acoustic wave to electric transducer is disposed on another portion of the upper surface of the piezoelectric SAW loss reduction film layer.

In still another embodiment, the SAW biofilm sensor may further include a substrate defining an upper surface and a lower surface, wherein the lower surface of the piezoelectric SAW loss reduction film layer is disposed on the upper surface of the substrate.

In yet another embodiment, a portion of the lower surface of the piezoelectric film layer is disposed on a portion of the upper surface of the piezoelectric SAW loss reduction film layer and disposed between the transmitting electric to acoustic wave transducer and the receiving acoustic wave to electric transducer.

In a still further embodiment, another portion of the lower surface of the piezoelectric film layer may be disposed between the transmitting electric to acoustic wave transducer and the receiving acoustic wave to electric transducer.

In one embodiment of the SAW biofilm sensor, wherein the piezoelectric layer defines an upper sub-layer and a lower sub-layer, wherein the lower sub-layer defined by the portion of the lower surface of the piezoelectric film layer is disposed on the portion of the upper surface of the lower piezoelectric film layer and is disposed between the transmitting electric to acoustic wave transducer and the receiving acoustic wave to electric transducer. The upper sub-layer is defined by the portion of the piezoelectric layer between the passivation film layer and the lower sub-layer. The lower sub-layer has a shear modulus and density to define a first SAW velocity. The upper sub-layer has a shear modulus and density to define a second SAW velocity wherein the second velocity differs from the first velocity.

In one embodiment, the second velocity is equal to or greater than the first velocity.

In still another embodiment, the SAW biofilm sensor the passivation layer includes aluminum oxide, $Al_2O_3$. In one embodiment, the passivation layer defines a thickness between the upper surface of the passivation layer and the lower surface of the passivation layer wherein the thickness of the passivation layer has a dimension of at least 45 nanometers (nm).

In yet another embodiment, the piezoelectric layer may include zinc oxide, ZnO. In one embodiment, the piezoelectric layer defines a thickness between the upper surface of the piezoelectric layer and the lower surface of the piezoelectric layer and the thickness of the piezoelectric layer has a dimension of at least 40 nanometers (nm).

The present disclosure relates also to a method of assembling a biofilm surface acoustic wave (SAW) sensor that includes depositing a piezoelectric layer on a SAW transducer electrode pattern and depositing a passivation layer on the piezoelectric layer.

In one embodiment, the depositing of the piezoelectric layer may include depositing a layer of zinc oxide ZnO on the SAW transducer electrode pattern. In a still further embodiment, the depositing a layer of zinc oxide ZnO on the SAW transducer electrode pattern may include depositing a layer of zinc oxide ZnO having a thickness of at least 40 nanometers (nm).

In yet another embodiment, the depositing a passivation layer on the piezoelectric layer may include depositing a layer of aluminum oxide $Al_2O_3$ on the piezoelectric layer.

In a still further embodiment, the depositing of the layer of aluminum oxide $Al_2O_3$ on the piezoelectric layer may include depositing a layer of aluminum oxide $Al_2O_3$ having a thickness of at least 45 nanometers (nm) on the piezoelectric layer.

In one embodiment, the method of assembling may further include depositing the SAW transducer electrode pattern on a piezoelectric SAW loss reduction film layer. The method may further include depositing the piezoelectric SAW loss reduction film layer on a substrate.

In another embodiment, the step of depositing the piezoelectric layer on the SAW transducer electrode pattern includes pulsed laser deposition.

In still another embodiment, the step of depositing the passivation layer on the piezoelectric layer includes atomic layer deposition.

BRIEF DESCRIPTION OF THE DRAWINGS

These and other advantages will become more apparent from the following detailed description of the various embodiments of the present disclosure with reference to the drawings wherein:

FIG. 4A illustrates a top perspective schematic view of an exemplary embodiment of the SAW biofilm sensor of FIGS. 2 and 3 according to one embodiment of the present disclosure that includes the piezoelectric SAW transducer of FIG. 2 further including a piezoelectric layer and a passivation layer disposed on the upper surface of the SAW transducer and further illustrating a SAW passing through a biofilm on the upper surface of the passivation layer;

FIG. 4B illustrates a cross-sectional schematic view of the SAW biofilm sensor of FIG. 4A illustrating the piezoelectric transducer and the thickness dimensions of the piezoelectric layer, the passivation layer and the biofilm;

FIG. 7A is a schematic illustration of a piezoelectric SAW loss reduction film layer deposited on a substrate;

FIG. 7B is a schematic diagram of an interdigitated piezoelectric SAW transducer electrode pattern deposited on the piezoelectric SAW loss reduction film layer of FIG. 7A;

FIG. 7C is a schematic diagram of a piezoelectric layer deposited on the electrode pattern and the piezoelectric SAW loss reduction film layer deposited on a substrate of FIGS. 7A and 7B;

FIG. 7D is a schematic diagram of the piezoelectric layer and electrode pattern of FIG. 7C undergoing annealing;

FIG. 7E is a schematic diagram of a passivation layer deposited partially on the electrode pattern of FIGS. 7B, 7C and 7D and on the piezoelectric layer of FIGS. 7C and 7D;

DETAILED DESCRIPTION

The present disclosure relates to the design of a passivated piezoelectric SAW transducer biofilm sensor according to embodiments of the present disclosure without loss of sensitivity for biosensing applications.

Figure 1:
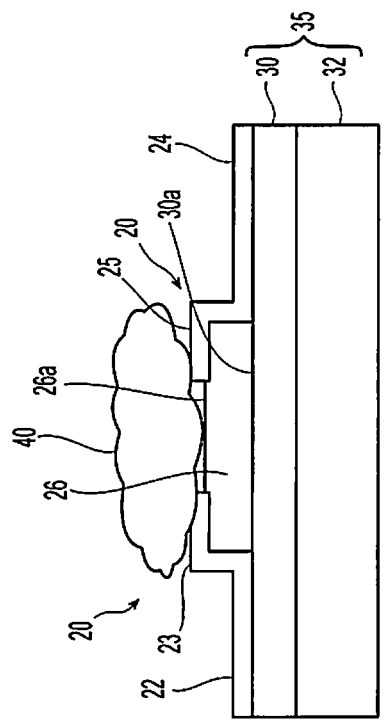
FIG. 1 illustrates a cross-sectional view of an example of a coated piezoelectric SAW transducer according to the prior art.

First, to illustrate the advantages of the embodiments of the present disclosure, FIG. 1 illustrates an example of a prior art SAW biofilm sensor 10 wherein the piezoelectric materials used in the SAW biofilm sensor can be dissolved due to long term exposure to liquid. More particularly, SAW biofilm sensor 10 includes a SAW transducer 20 having a transmitting electrode transducer 22 and a receiving electrode transducer 24 each mounted over a common piezoelectric loss reduction film 30 and a substrate 32. The common piezoelectric loss reduction film 30 and substrate 32 form a transducer mounting structure 35. The transmitting electrode transducer 22 includes an elevated portion 23 and the receiving electrode transducer 24 includes a corresponding interfacing elevated portion 25 which are each raised above upper surface 30a of the common piezoelectric loss reduction film 30. Both the elevated portion 23 and the elevated portion 25 are elevated above, and not in contact with, the upper surface 30a to provide a space above the common piezoelectric loss reduction film 30 for a thin film 26 in contact with, and mounted over, the common piezoelectric loss reduction film 30. The elevated portions 23 and 25 each extend partially over upper surface 26a of the thin film 26. During usage, a biofilm 40 is positioned over both the elevated portions 23 and 25 and upper surface 26a of the thin film 26.

The substrate 32 may be made from silicon Si and the common piezoelectric loss reduction film 30 may be made from silicon dioxide $SiO_2$.

Since the biofilm 40 is in direct contact with the elevated portions 23 and 25 of the transmitting electrode transducer 22 and the receiving electrode transducer 24, respectively, the configuration of a SAW sensor such as SAW sensor 10 in FIG. 1 has been shown to be susceptible to dissolution of the common piezoelectric film 30 due to long term exposure to the liquid biofilm.

In contrast, the present disclosure relates to a successfully passivated ZnO based SAW sensor for long term biofilm growth monitoring in an animal serum or bacterial growth media. Atomic Layer Deposition (ALD) was applied for high density and conformal aluminum oxide ($Al_2O_3$) film deposition to protect the ZnO of the SAW sensor from media. The SAW sensor was used for the in vitro real time study of *E. coli* static biofilm growth in Lysogeny Broth (LB) media and in 10% Fetal Bovine Serum (FBS), the latter of which is the most widely used serum for mammalian cell culture due to similarities to in vivo environments [28].

The remainder of the present disclosure presents the design of the inverted SAW sensor for the targeted mode of the wave and fabrication process. The material and experimental procedures for biofilm detection in the sensor are presented. The results show the biofilm detection using the sensor in consecutive testing both in bacterial growth media and animal serum.

Figure 2:
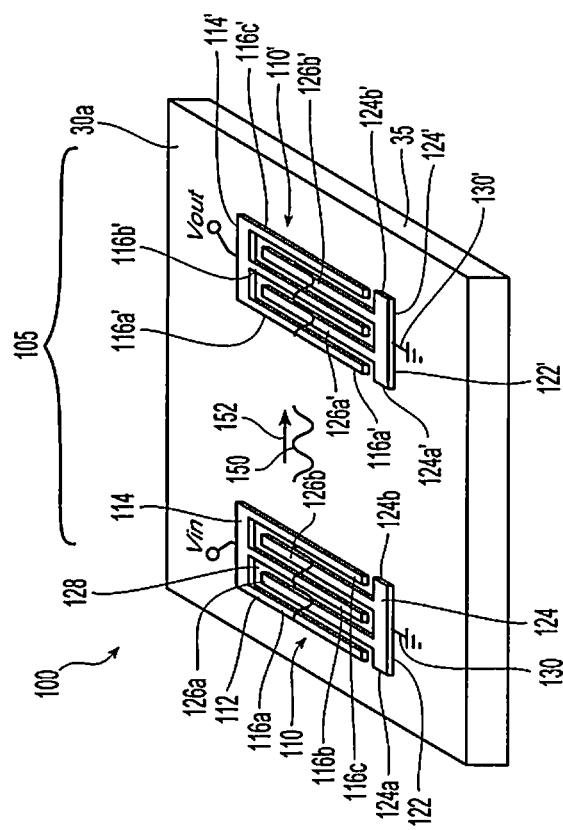
FIG. 2 illustrates a top perspective view of an exemplary embodiment of an uncoated piezoelectric SAW transducer within a piezoelectric substrate that is utilized to receive a passivation film according to one embodiment of the present disclosure.

More particularly, FIG. 2 illustrates a top perspective view of an exemplary embodiment of an uncoated piezoelectric SAW transducer 100 having a transmitting electric to acoustic wave transducer 110 and a receiving acoustic wave to electric transducer 110' both mounted on upper surface 30a of the transducer mounting substrate 35 of FIG. 1 that is utilized to receive a passivation film according to one embodiment of the present disclosure. The transmitting electric to acoustic wave transducer 110 and the receiving acoustic wave to electric transducer 110' together define an interdigitated SAW transducer 105 as is known in the art. The transmitting electric to acoustic wave transducer 110 includes a first transmitting electrode comb-like or prong-like electrically conductive member 112 that interlocks or interdigitates with a second transmitting electrode comb-like electrically conductive member 122. The first transmitting conductive member 112 includes a rectangularly-shaped base 114 from which extend orthogonally first rectangularly-shaped peripheral prong 116a, rectangularly-shaped central prong 116b and second rectangularly-shaped peripheral prong 116c.

As noted, the transmitting electric to acoustic wave transducer 110 also includes the second transmitting electrode comb-like or prong-like electrically conductive member 122 that interlocks or interdigitated with the first transmitting electrode comb-like electrically conductive member 112. The second transmitting conductive member 122 includes a rectangularly-shaped base 124 from which extend orthogonally first rectangularly-shaped prong 126a and second rectangularly-shaped prong 126b. The rectangularly shaped base 124 defines a first end 124a and a second end 124h. The first prong 126a is positioned at a distance away from first end 124a and the second prong 1261 is positioned at a distance away from the second end 126b to define a central rectangularly-shaped aperture 128 between the first prong 126a and the second prong 126b.

The first transmitting electrically conductive member 112 includes a voltage input terminal Vin that is in direct electrical communication with, for example, the rectangularly-shaped base 114 such that the entire first transmitting electrically conductive member 112 is in electrical communication with the voltage input terminal Vin. The first and second electrically conductive members 112 and 122 are arranged such that the prongs 116a, 116b, 116c are adjacent to and intermesh with prongs 126a and 126h. The second transmitting electrically conductive member 122 includes a ground terminal 130 that is in direct electrical communication with, for example, the rectangularly-shaped base 124 such that the entire second transmitting electrically conductive member 122 is in electrical communication with the ground terminal 130.

The receiving acoustic wave to electric transducer 110' includes the same components as, and is arranged in the same manner as, transmitting electric to acoustic wave transducer 110 and for convenience the components are designated with primes.

Consequently, receiving acoustic wave to electric transducer 110' includes a first transmitting electrode comb-like or prong-like electrically conductive member 112' that interlocks or interdigitates with a second transmitting electrode comb-like electrically conductive member 122'. The first receiving electrically conductive member 112' includes rectangularly-shaped base 114 from which extend orthogonally first rectangularly-shaped peripheral prong 116a', rectangularly-shaped central prong 116b' and second rectangularly-shaped peripheral prong 116c'.

The receiving electric to acoustic wave transducer 110' also includes the second receiving electrode comb-like or prong-like electrically conductive member 122' that interlocks or interdigitates with the first receiving electrode comb-like electrically conductive member 112'. The second receiving conductive member 122' includes a rectangularly-shaped base 124' from which extend orthogonally first rectangularly-shaped prong 126a' and second rectangularly-shaped prong 126b'. The rectangularly-shaped base 124' defines a first end 124a' and a second end 124b'. The first prong 126a' is positioned at a distance away from first end 124a' and the second prong 126b' is positioned at a distance away from the second end 126b' to define a central rectangularly-shaped aperture 128' between the first prong 126a' and the second prong 126b'.

The first receiving electrically conductive member 112' includes a voltage output terminal Vout that is in direct electrical communication with, for example, the rectangularly-shaped base 114' such that the entire first receiving electrically conductive member 112' is in electrical communication with the voltage output terminal Vout. The first and second electrically conductive members 112' and 122' are arranged such that the prongs 116a', 116b', 116c' are adjacent to and intermesh with prongs 126a' and 126h'. The second receiving electrically conductive member 122' includes a ground terminal 130' that is in direct electrical communication with, for example, the rectangularly-shaped base 124' such that the entire second receiving electrically conductive member 122' is in electrical communication with the ground terminal 130'.

When a voltage source, not shown, is placed across the terminals Vin and Vout, a surface acoustic wave 150 is generated by the transmitting electric to acoustic wave transducer 110 and travels in the direction of arrow 152 towards the receiving acoustic wave to electric transducer 110'.

Figure 3:
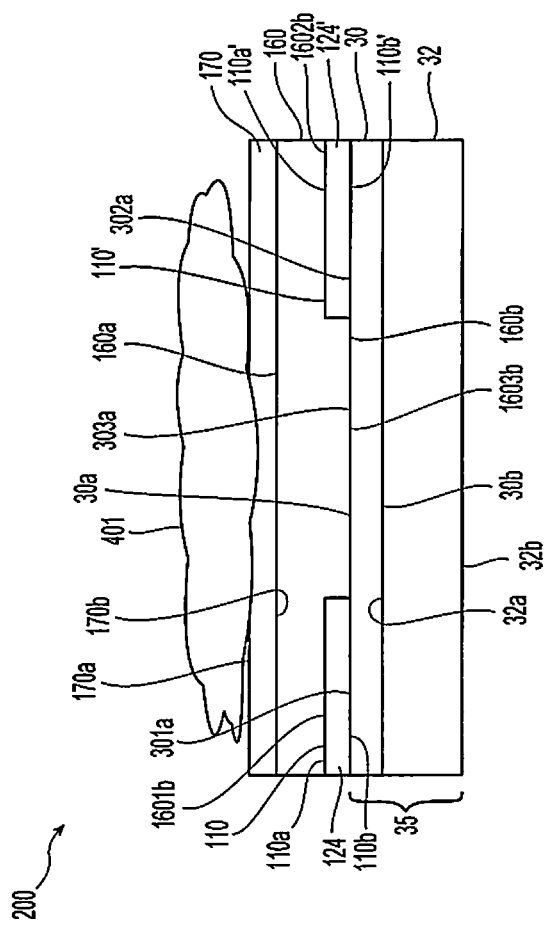
FIG. 3 illustrates a cross-sectional view of a coated piezoelectric SAW transducer biofilm sensor according to one embodiment of the present disclosure.

FIG. 3 illustrates a cross-sectional view of a coated piezoelectric SAW transducer biofilm sensor 200 according to one embodiment of the present disclosure. More particularly, surface acoustic wave (SAW) biofilm sensor 200 includes the interdigitated SAW transducer 105 of FIG. 2. Accordingly, the SAW biofilm sensor 200 includes transmitting electric to acoustic wave transducer 110 defining an upper surface 110a and a lower surface 110b where the cross-section (not shown) is taken through the rectangularly-shaped base 124. The surface acoustic wave (SAW) biofilm sensor 200 also includes receiving acoustic wave to electric transducer 110' defining an upper surface 110a' and a lower surface 110b'.

The lower surface 110a of the transmitting electric to acoustic wave transducer 110 is disposed on a portion 301a of the upper surface 30a of the piezoelectric SAW loss reduction film layer 30 and the lower surface 110a' of the receiving acoustic wave to electric transducer 110' is disposed on another portion 302a of the upper surface 30a of the piezoelectric SAW loss reduction film layer 30.

A piezoelectric film layer 160 defines an upper surface 160a and a lower surface 160b. A portion 1601b of the lower surface 160b of the piezoelectric film layer 160 is disposed on the upper surface 110a of the transmitting electric to acoustic wave transducer 110. Another portion 1602b of the lower surface 160b of the piezoelectric film layer 160 is disposed on the upper surface 110'a of the receiving acoustic wave to electric transducer 110'.

A passivation film layer 170 defines an upper surface 170a and a lower surface 170b. The lower surface 170b of the passivation film layer 170 is disposed on the upper surface 160a of the piezoelectric film layer 160. Thus, the upper surface 160a of the passivation film layer 170 is thereby configured to enable contact with a biofilm 40.

In a similar manner as described with respect to FIG. 1, the coated piezoelectric SAW transducer biofilm sensor 200 may be disposed or mounted on transducer mounting structure 35 which include common piezoelectric loss reduction film layer 30 and substrate 32. The substrate 32 defines an upper surface 32a and a lower surface 32b. Similarly, the common piezoelectric loss reduction film layer 30 defines the upper surface 30a and a lower surface 30b. The lower surface 30b of the piezoelectric SAW loss reduction film layer 3030 is disposed on the upper surface 32a of the substrate 32.

A portion 1603b of the lower surface 160b of the piezoelectric film layer 160 is disposed on a portion 303a of the upper surface 30a of the piezoelectric SAW loss reduction film layer 30 and disposed between the transmitting electric to acoustic wave transducer 110 and the receiving acoustic wave to electric transducer 110'.

FIG. 4A illustrates a top perspective schematic view of the exemplary embodiment of the SAW biofilm sensor 200 of FIGS. 2 and 3 according to one embodiment of the present disclosure that includes the piezoelectric SAW transducer 105 further including the piezoelectric layer 160 and the passivation layer 170 disposed on the upper surfaces 110a and 110a' of the SAW transducer 105 and further illustrating a SAW 150 passing in the direction of arrow 152 through a biofilm 40 on the upper surface 170a of the passivation layer 170.

FIG. 4B illustrates a cross-sectional schematic view of the SAW biofilm sensor 200 of FIG. 4A illustrating the piezoelectric transducer 105 and the thickness dimensions of the piezoelectric layer 160, the passivation layer 170 and the biofilm 40. More particularly, in the exemplary embodiment of FIG. 4B, the piezoelectric layer 160 may define an upper sub-layer 162 and a lower sub-layer 161 which together define thickness d of the piezoelectric layer 160.

The lower sub-layer 161 is defined by the portion 1603b of the lower surface 160b of the piezoelectric film layer 160 that is disposed on the portion 303a of the upper surface 30a of the lower piezoelectric film layer 30 and is disposed between the transmitting electric to acoustic wave transducer 110 and the receiving acoustic wave to electric transducer 110'. The upper sub-layer 162 is defined by the portion of the piezoelectric layer 160 between the passivation film layer 170 and the lower sub-layer 161 of the piezoelectric layer.

The lower sub-layer 161 has a shear modulus and density to define a first SAW velocity V1. The upper sub-layer 162 has a shear modulus and density to define a second SAW velocity V2. Although the second velocity V2 may differ from the first velocity V1, for the purposes of simplifying the design analysis, the two velocities may be set equal to one another. Alternatively, the second velocity V2 may be equal to or greater than the first velocity V1.

The passivation layer 170 defines a thickness h between the upper surface 160a of the passivation layer 160 and the lower surface 160b of the passivation layer 160 while the biofilm 40 defines a thickness x.

In one embodiment, the piezoelectric layer 160 includes zinc oxide, ZnO and the thickness d of the piezoelectric layer 160 has a dimension of at least 40 nanometers (nm).

In one embodiment, the passivation layer includes aluminum oxide, $Al_2O_3$, and the thickness h of the passivation layer 170 has a dimension of at least 45 nanometers (nm).

The specific design for the selection of the material and thickness of the piezoelectric layer 160 and the passivation layer 170 is described in more detail below.

Materials and Methods
Design of the SAW Sensor

For applications of a SAW sensor in liquid environments, selecting the proper mode of propagation is crucial to prevent severe attenuation or the wave. In a SAW sensor, the surface of the piezoelectric layers is set to a high frequency oscillation governed by the design of the interdigitated transducers (IDT) and the SAW velocity of the piezoelectric material. This no-load oscillation frequency is affected by environmental changes at the surface of the SAW sensor. These effects are observed experimentally as changes in resonant frequency, representing a shift in the SAW phase velocity. However, one of the challenges for biosensor applications is the extremely high attenuation damping of the SAW in liquid environments, when Rayleigh mode waves are generated. In this mode the acoustic wave displacement is perpendicular to the surface and causes significant attenuation of the oscillations in liquid environments. Unlike Rayleigh mode waves, Love mode SAW generation demonstrates displacement planar to the surface and the oscillations are not attenuated in liquid environments [11-15, 18-20, 29-31]. The generation of Love or Rayleigh mode waves depends on the crystallographic orientation of the piezoelectric film. Therefore, it is highly advantageous to deposit piezoelectric material with a specific orientation for generating Love mode SAW [16-22, 29-31]. ZnO with a high piezoelectric coefficient is capable of generating very high frequency (GHz, gigahertz, where Hz is hertz or 1 cycle/sec) SAW, and it has been shown to grow along the crystallographic orientation that favors Love mode propagation on a $SiO_2$/Si substrate [19-22]. Love mode waves are predominantly generated with the SAW IDT aligned perpendicular to the c-axis of the ZnO film [16-22].

Some important parameters, such as the SiO.sub.2 thickness, the IDT electrode dimensions, and the ZnO deposition method, had to be considered in the design of a highly sensitive SAW sensor. In order to confine the propagation of the SAW on the surface of the device, a thin film that can prevent acoustic wave loss from the piezoelectric material to Si substrate was required between ZnO film and Si. $SiO_2$ was previously shown [15, 18] to be an appropriate loss blocking film for thicknesses around 50 nm and was selected in this work. For the best resonance of the SAW at the designed operational frequency, the IDT separation d should be equal to half of the operational wavelength λ. (See FIG. 7B). The acoustic wave velocity for the ZnO thin film used in this work was 4814 m/s, and the operational frequency (401 MHz-406 MHz) of the SAW sensor was designed to meet the regulation set by the Federal Communication Commission (FCC) for future biomedical biofilm detection applications [32, 48]. This wavelength (λ) was 12 μm, rendering the electrode separation of the IDT 6 μm (λ/2). The crystal quality of ZnO film also had to be high for a sensitive SAW sensor. The ZnO film with low impurities and lattice defects was achieved by PLD which has been widely used in metal oxides for high quality film deposition due to stoichiometric deposition with the target material [33] and a relatively simple set-up.

To achieve advantages over prior art biofilm sensors for biofilm detection, it was necessary to provide an inverted structure for the saw sensor 200, as shown in FIGS. 3, 4A and 4B as compared to the structure of a standard SAW sensor such as biofilm sensor 20 as shown in FIG. 1. In traditional SAW sensors such as biofilm sensor 20, the IDT is exposed to the liquid environment directly, causing IDT corrosion in long term studies. However, in the inverted SAW sensor 200 according to FIGS. 3, 4A and 4B, the IDT lifetime is extended because the IDT is patterned under the piezoelectric film. The sensitivity of the Love mode SAW sensor in the top and bottom of piezoelectric films also show the same level of sensitivity for our designed ZnO film thickness (400 nm) based on the Love mode propagation depth [11-14, 29].

The material of the IDT, traditionally aluminum in the SAW sensor, can be selected by the acoustic impedance match theory [34]. Potential materials, such as aluminum and gold, were selected and the acoustic power reflective coefficient (R) was calculated based on the theory. The reflective coefficient of the aluminum and gold were 0.058 and 0.012 respectively. The lower reflective coefficient in IDT represents more energy transmission to the piezoelectric material which makes a highly sensitive SAW sensor. Therefore, the IDT material was chosen to be gold based on the low R value.

Selection of Passivation Film

Since the bare ZnO layer 160 without a passivation film layer 170 was damaged both in LB media and 10% FBS, selection of the proper material to protect ZnO while considering future biomedical applications is important to maintain the sensitivity of the sensor. The sensitivity of the passivated SAW sensor is decreased as compared to the unpassivated sensor due to the initial mass loading and dispersion of the wave in the passivation film [12, 29, 35-40]. To investigate the effect of the added material on the SAW sensitivity in addition to the material selection, we consider only the mass loading effect of the passivation film based on the assumption that the dispersion in the passivation film is minimal due to a much thinner passivation layer (45 nm) as compared to the wavelength of the SAW [35, 38, 40]. As noted, the schematic cross section view of the inverted passivation SAW sensor 200 is shown in FIGS. 3, 4A and 4B. The sensitivity of the SAW sensor ($S_m^v$) is directly proportional to the velocity change due to the mass loading as shown in equation (1) [15, 18-20].

$$S_m^v = \lim_{\Delta m \to 0} \frac{1}{\Delta m}\left(\frac{\Delta v}{v_0}\right) \quad (1)$$

where $v_0$ is the initial velocity of the wave, m is the amount of the additional mass, and $\Delta v$ is the wave velocity changes due to $\Delta m$. The SAW velocity (v), shown in equation (2), is defined by the shear modulus of the piezoelectric material and local area density based on the one-dimensional acoustic wave equation (3) [15, 18-20].

$$v = \sqrt{\frac{C}{\rho}} \quad (2)$$

$$\frac{\partial^2 u}{\partial t^2} = \left(\frac{C}{\rho}\right)\frac{\partial^2 u}{\partial y^2} \quad (3)$$

where C is the shear modulus of the surface material, u is the mechanical displacement of the piezoelectric substrate, $\rho$ is material density of the surface, y is the axis of the mechanical displacement propagation, and v is the velocity of the SAW in equations (2) and (3). In order to simplify the modeling of passivation effects on the sensitivity of the SAW sensor, the bacterial growth over the sensor was assumed uniform, so that bacterial mass loading only depended on the thickness of the biofilm. Based on this assumption, the sensitivity of the SAW sensor from equation (1) was proportional to the velocity change as biofilm thickness (x) approaches zero as shown in equation (4).

$$S_m^v \propto \frac{dv}{dx_{x \to 0}} \quad (4)$$

The biofilm formed on the sensor also has a comparatively low shear modulus that can be neglected in the calculation of the total shear modulus of the passivated SAW sensor. The total shear modulus including the ZnO and the passivation film was calculated based on a mechanical spring series connection because the SAW is transferred from ZnO film to the passivation layer sequentially. Based on the assumptions and the total shear modulus calculation, the SAW velocity on a sensor coated with a biofilm was determined by the following equation (5).

$$v = \sqrt{\frac{C_{ZnO}}{\rho_{ZnO}d}\left(\frac{C_{film}}{C_{ZnO}+C_{film}}\right)\left(\frac{1}{1+\frac{\rho_{film}h}{\rho_{ZnO}d}+\frac{\rho_{bac}x}{\rho_{ZnO}}}\right)} \quad (5)$$

where $C_{film}$ and $C_{Zno}$ are the shear moduli of the passivation film and ZnO, $\rho_{Zno}$ and $\rho_{film}$ are the densities of the ZnO and passivation film, h is the thickness of the passivation film, d is the thickness of the ZnO film, and x is the biofilm thickness. All parameters except the biofilm thickness (x) were determined by selecting potential passivation materials (i.e. $Al_2O_3$, $Si_3N_4$, $SiO_2$ and Teflon) and their thicknesses which were assumed to be 40 nm for all passivation films considered. Potential passivation materials with mechanical properties similar to the ZnO film, such as shear modulus and density, were selected [41, 42]. The sensitivity of the SAW sensor with different passivation films was calculated by differentiating equation (5) with respect to x, and letting x approach zero, based on equation (4).

Figure 8:
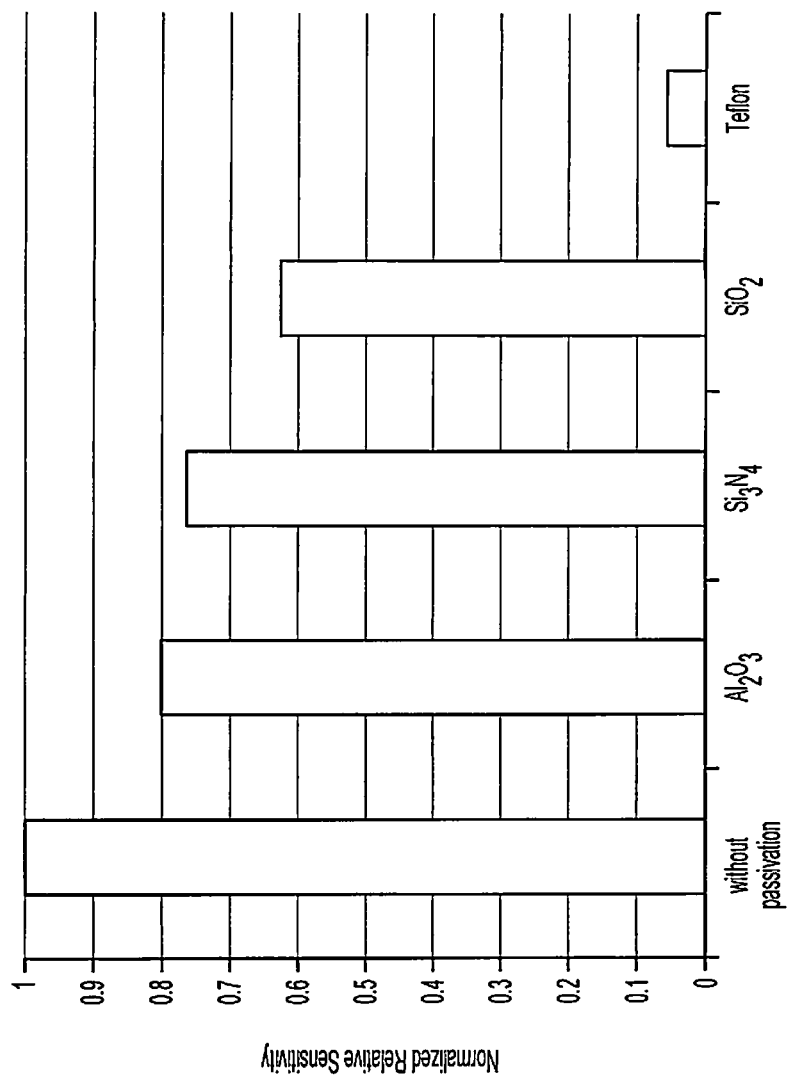
FIG. 8 is a graphical plot of normalized sensitivity of a SAW biofilm sensor assembled in accordance with FIGS. 2-7E for various passivation layer materials including without passivation.

FIG. 8 graphically illustrates the normalized theoretical sensitivity for, from left to right, without passivation, aluminum oxide —$Al_2O_3$, silicon nitride —$Si_3N_4$, silicon dioxide —$SiO_2$, and Teflon. The lowest degradation in sensitivity is observed for the $Al_2O_3$ passivation layer with a 0.20 reduction, while Teflon had the maximum degradation at 0.95 reduction.

The application of this fundamental theoretical treatment showed that an $Al_2O_3$ film was best suited as a passivation layer and it was selected. The thickness of the passivation film (h) in equation (5) is important for our application. The film should be thick enough for effective passivation, but should not be too thick that the added layer causes a significant attenuation both due to mass loading and dispersion of the SAW resulting in substantial loss in sensitivity. The minimum required thickness of $Al_2O_1$ film (45 nm) was empirically determined. The detailed studies were presented in the film characterization section.

Fabrication

Figure 5:
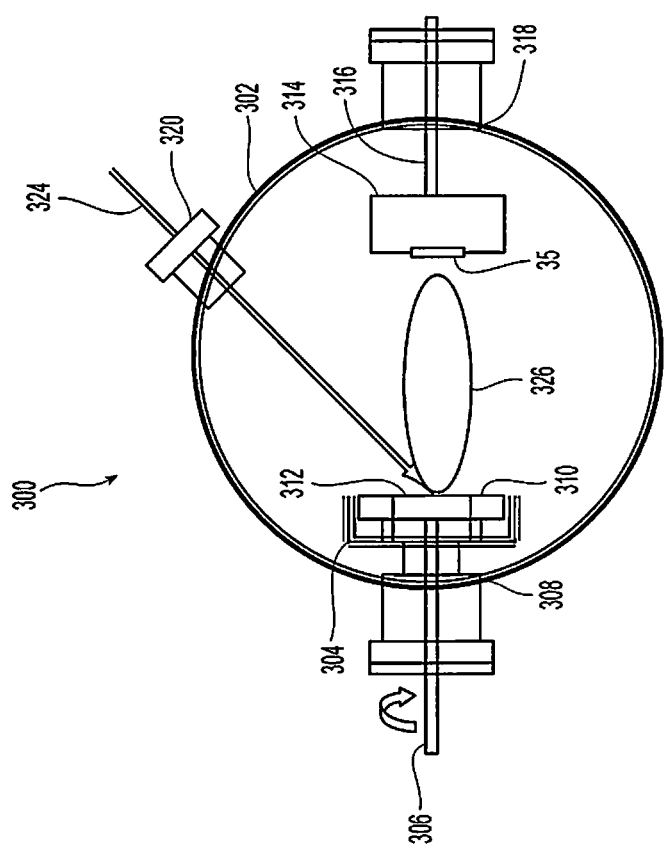
FIG. 5 illustrates a schematic diagram of pulsed layer deposition of the piezoelectric layer on a substrate for assembling the piezoelectric SAW biofilm sensor of FIGS. 2, 3, 4A and 4B.

As described below in more detail with respect to FIG. 5, to create the piezoelectric layer 160 on the transducer mounting structure 35, the target material employed herein is zinc oxide, ZnO. Stoichiometric film deposition is achieved by application of a 248 nm KrF laser in 25 ns pulses at 250° C.

Figure 6:
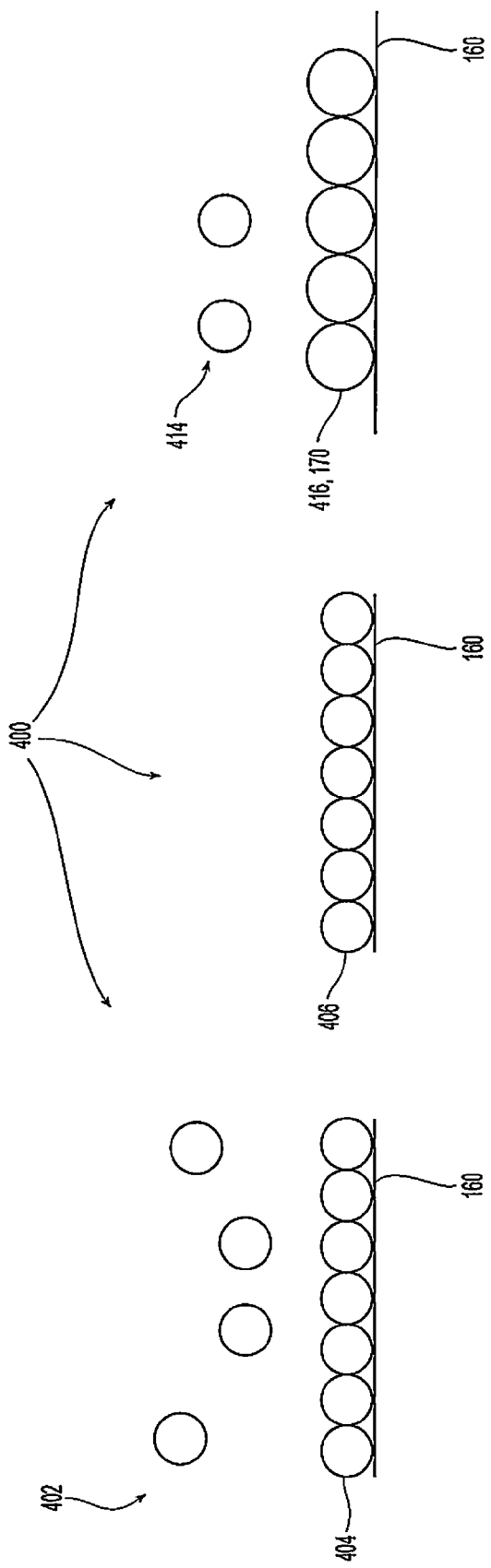
FIG. 6 illustrates a schematic diagram of atomic layer deposition of the passivation layer of FIGS. 3, 4A and 4B.

FIG. 6 illustrates a schematic diagram of atomic layer deposition of the passivation layer 170 of FIGS. 3, 4A and 4B.

The fabrication process flow is shown in FIGS. 7A through 7E. Referring first to FIG. 7A, a silicon dioxide ($SiO_2$) layer 30 was deposited on the upper surfaces 32a of (100) Si substrates 32 by low pressure chemical vapor deposition (LPCVD) as studied in [15, 22].

Referring to FIG. 7B, the IDT 105 was patterned using traditional photolithography before depositing the piezoelectric layer 160, e.g., ZnO film. The IDT prongs 116a and 116a' are deposited to have a width W1 of 1 µm (microns), prongs 116b and 116b' are deposited to have a width W2 of 1.5 µm, and prongs 116c and 116c' are deposited to have a width W3 of 2 µm. Due to the small feature size of the IDT 105, including 1 µm, 1.5 µm, and 2 µm wide electrodes, oxygen plasma was used to remove residual photoresist after development.

In FIG. 7C, Cr/Au (15 nm/200 nm) as the IDT 105 material was deposited on the wafer or transducer mounting structure 35 by E-beam evaporation, followed by lift-off. The transducer mounting structure 35 was diced into smaller segments before deposition of the piezoelectric layer 160, composed of ZnO, was performed by pulsed laser deposition (PLD). Crystalline [001] orientation ZnO films on $SiO_2$/(100)Si substrates were grown by PLD. The piezoelectric layer 160 did not entirely cover the IDT 105 such that an indentation 162a from longitudinal external edge 1161a of the prong 116a and an indentation 162b from longitudinal external edge 1162c' of the prong 116c' were formed in the piezoelectric layer 160 to subsequently accommodate portions of the passivation layer 170.

FIG. 7D illustrates the annealing process of the ZnO film pattern wherein the ZnO film pattern was annealed at 800° C. for 1 hour.

FIG. 7E is a schematic diagram of passivation layer 170 deposited partially on the electrode pattern 105 of FIGS. 7B, 7C and 7D and on the piezoelectric layer 160 of FIGS. 7C and 7D. Vertical edges 172a, 172b of the passivation layer 170 are formed by the atomic layer deposition to fill the indentations 162a, 162b, respectively, of the piezoelectric layer 160.

For simplicity, in FIGS. 7B to 7E, only the prongs 116a, 116b, 116c of the first transmitting electrically conductive member 112 and only the prongs 116a', 116b', 116c' of the first receiving electrically conductive member 112' as shown in FIG. 2 are illustrated. The second transmitting electrically conductive member 122 and the second receiving electrically conductive member 122' are omitted in FIGS. 7B to 7E.

Returning to FIG. 5, there is illustrated a schematic diagram of a pulsed layer deposition (PLD) system for the piezoelectric layer 160 on the transducer mounting structure 35 that includes common piezoelectric loss reduction layer 30 and substrate 32 for assembling the piezoelectric SAW biofilm sensor 200 of FIGS. 2, 3, 4A and 4B. More particularly, pulsed laser deposition (PLD) system 300 includes a vacuum chamber 302 having a rotating target carousel 304. The carousel is rotatable by a first shaft 306 which passes through a first penetration 308 in the vacuum chamber 302. The shaft 306 rotates a platform 310 supported on the target carousel 304 and supports the target 312 which is thus capable of being rotated by the first shaft 306.

The transducer mounting structure 35 is positioned directly opposite to the target 312 on the target platform 310 and the target carousel 304. The structure 35 is positioned on a heatable sample stage 314 that is supported by a second shaft 316 that passes through a second penetration 318 in the vacuum chamber 302.

A quartz window 320 is positioned in the vacuum chamber 302 at an angle to enable a beam of laser light 324 to impact the target 312. As a result of the beam of laser light 324 impacting the target 312, a plume 326 of target material is created within the vacuum chamber and deposits on the transducer mounting structure 35 which includes substrate 32.

The laser deposition system used a KrF excimer laser at a wavelength of 248 nm with pulse duration of 25 ns to ablate a high purity (99.99%) ZnO ceramic target. The ZnO layer was grown at 250° C. with an ambient oxygen partial pressure of ~$1.0 \times 10^{-4}$ Torr. After ZnO film deposition, electrical contact pad areas were patterned by photolithography and the ZnO was etched using a solution that consisted of phosphoric acid, acetic acid, and deionized water (1:1:30).

As shown in FIG. 7D, the partially completed biofilm sensor 200 was annealed at 800° C. for one hour to increase the resistivity of the ZnO [43]. After annealing, the resistance measured in the IDT increased from 150Ω to 30-40 MΩ. As compared to FIG. 7C, there are generally no dimensional changes for the piezoelectric layer 160, the electrode pattern 105 or the transducer mounting structure 35 as a result of the annealing process.

FIG. 6 is a schematic illustration of a gas-based flow ALD process 400 to cause the passivation. FIG. 7E is a schematic diagram of the passivation layer 170 deposited partially on the electrode pattern of FIGS. 7B, 7C and 7D and on the piezoelectric layer 160 of FIGS. 7C and 7D. Referring now to FIG. 6 and FIG. 7E, the ZnO surface 160a of the SAW sensor 200 may be passivated by depositing an $Al_2O_3$ film using atomic layer deposition (ALD. To deposit the passivation layer 170, $Al_2O_3$ ALD thin films were fabricated at 150° C. in a flow-through chamber of a Beneq Model TFS-500 atomic layer deposition reactor system (available from Beneq Oy, Vantaa, Finland). As shown on the left side of FIG. 6, trimethylaluminum (TMA) $Al_2(CH_3)_3$, originating as a liquid precursor (not shown) that is converted to a vapor at 402 was introduced into the ALD reactor (not shown) and formed a single layer of the TMA 404 on the ZnO layer 160. In the center of FIG. 6, the single layer of the TMA 404 is purged of unbound TMA vapor to become a purged single layer 406 of the TMA. As shown on the right side of FIG. 6, water vapor ($H_2O$) 414 as the oxygen source was introduced into the ALD reactor and a covalent bonding between the TMA layer 406 and hydroxyl group of the water vapor 414 was established creating a single atomic layer of aluminum oxide 416 deposition. Each deposition cycle results in a 0.09 nm/cycle of deposition rate consistently. The single atomic layer of aluminum oxide $Al_2O_3$ 416 thus becomes the passivation layer 170. To illustrate that the TMA layer 406 has bonded with the hydroxyl group of the water vapor 414, the size of the circles representing the aluminum oxide $Al_2O_3$ 416 are shown to be larger than the size of the circles representing the TMA layer 406.

In view of the foregoing, those skilled in the art will understand that embodiments of the present disclosure relate to a surface acoustic wave (SAW) biofilm sensor 200 that includes SAW transducer 105, piezoelectric film layer 160, and passivation film layer 170. The piezoelectric film layer 160 is mounted over the SAW transducer 105 and the passivation film layer 170 is mounted over the piezoelectric film layer 160. In one embodiment, the passivation layer 170 includes aluminum oxide, $Al_2O_3$. In yet another embodiment, the passivation layer 170 defines a thickness h of at least nanometers (nm). In a still further embodiment, the piezoelectric layer 160 includes zinc oxide, ZnO. In yet another embodiment, the piezoelectric layer 160 defines a thickness d of at least 40 nanometers (nm).

Further, in view of the foregoing, those skilled in the art will understand that embodiments of the present disclosure relate to a method of assembling a biofilm surface acoustic wave (SAW) sensor, e.g., biofilm SAW sensor 200, that includes depositing a piezoelectric layer, e.g., piezoelectric layer 160, on a SAW transducer electrode pattern, e.g., IDT electrode pattern 105, and depositing a passivation layer, e.g., passivation layer 170, on the piezoelectric layer 160. The depositing a piezoelectric layer may include depositing a layer of zinc oxide ZnO on the SAW transducer electrode pattern 105. In one embodiment, the depositing a layer of zinc oxide ZnO on the SAW transducer electrode pattern 105 may include depositing a layer of zinc oxide ZnO having a thickness d of at least 40 nanometers (nm).

Further, the depositing a passivation layer, e.g., passivation layer 170, on the piezoelectric layer, e.g., piezoelectric layer 160, may include depositing a layer of aluminum oxide $Al_2O_3$ on the piezoelectric layer 160. The depositing a layer of aluminum oxide $Al_2O_3$ on the piezoelectric layer includes depositing a layer of aluminum oxide $Al_2O_3$ having a thickness h of at least 45 nanometers (nm) on the piezoelectric layer.

Additionally, the method of assembling the SAW biofilm sensor 200 may further include depositing the SAW transducer electrode pattern, e.g., IDT electrode pattern 105, on a piezoelectric SAW loss reduction film layer, e.g., piezoelectric SAW loss reduction film layer 30.

The method of assembling may further include depositing the piezoelectric SAW loss reduction film layer, e.g., piezoelectric. SAW loss reduction film layer 30, on a substrate, e.g. substrate 32.

The step of depositing a piezoelectric layer, e.g., piezoelectric layer 160, on a SAW transducer electrode pattern, e.g., IDT electrode pattern 105, may include pulsed laser deposition. Additionally, the step of depositing a passivation layer, e.g., passivation layer 170, on a piezoelectric layer, e.g., piezoelectric layer 160, may include atomic layer deposition.

Device Characterization and Testing

Before the SAW sensor was used to measure biofilm growth, the performance of the passivation film was characterized using an optical microscope to inspect the surface of the ZnO layer after exposure to growth media. The results were used to optimize the film thickness and fabrication process. The sensitivity of the sensor was studied by loading the sensor surface with &ionized (DI) water since its viscosity is negligible. After these characterization studies, the sensor response was tested using *E. coli* static biofilm growth.

$Al_2O_3$ Film Characterization

Based on the theoretical modeling calculation presented previously and the results shown in FIG. 8, $Al_2O_3$ was selected as a passivation film. $Al_2O_3$ films were deposited to thicknesses of 20 nm-45 nm by ALD to investigate the minimum required thickness for ZnO passivation. SAW sensors with four different thicknesses (20 nm, 30 nm, 40 nm, and 45 nm) of ALD $Al_2O_3$ film were placed in a LB media bacterial suspension for two days. The surface of the device was inspected using optical microscopy. As shown in FIGS. 9-12, visible ZnO damage was observed when the thickness of ALD $Al_2O_3$ was thinner than 45 nm.

Figure 9:
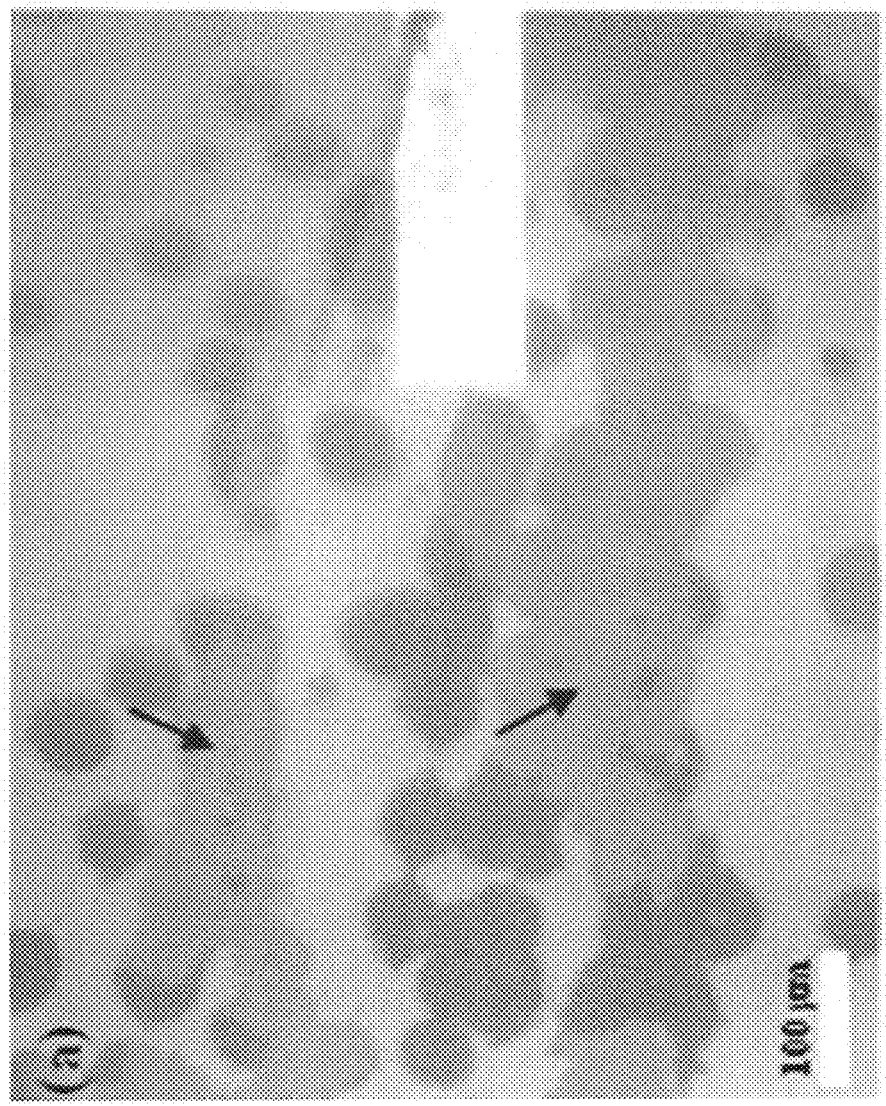
FIG. 9 is an optical microscopy image of a SAW biofilm sensor assembled in accordance with FIGS. 2-7E passivated by ALD of $Al_2O_3$ with a passivation layer thickness of 20 nanometers (nm) showing damaged areas.
Figure 10:
FIG. 10 is an optical microscopy image of another SAW biofilm sensor assembled in accordance with FIGS. 2-7E passivated by ALD of $Al_2O_3$ with a passivation layer thickness of 30 nm showing damaged areas.
Figure 11:
FIG. 11 is an optical microscopy image of yet another SAW biofilm sensor assembled in accordance with FIGS. 2-7E passivated by ALD of $Al_2O_3$ with a passivation layer thickness of 40 nm showing damaged areas.
Figure 12:
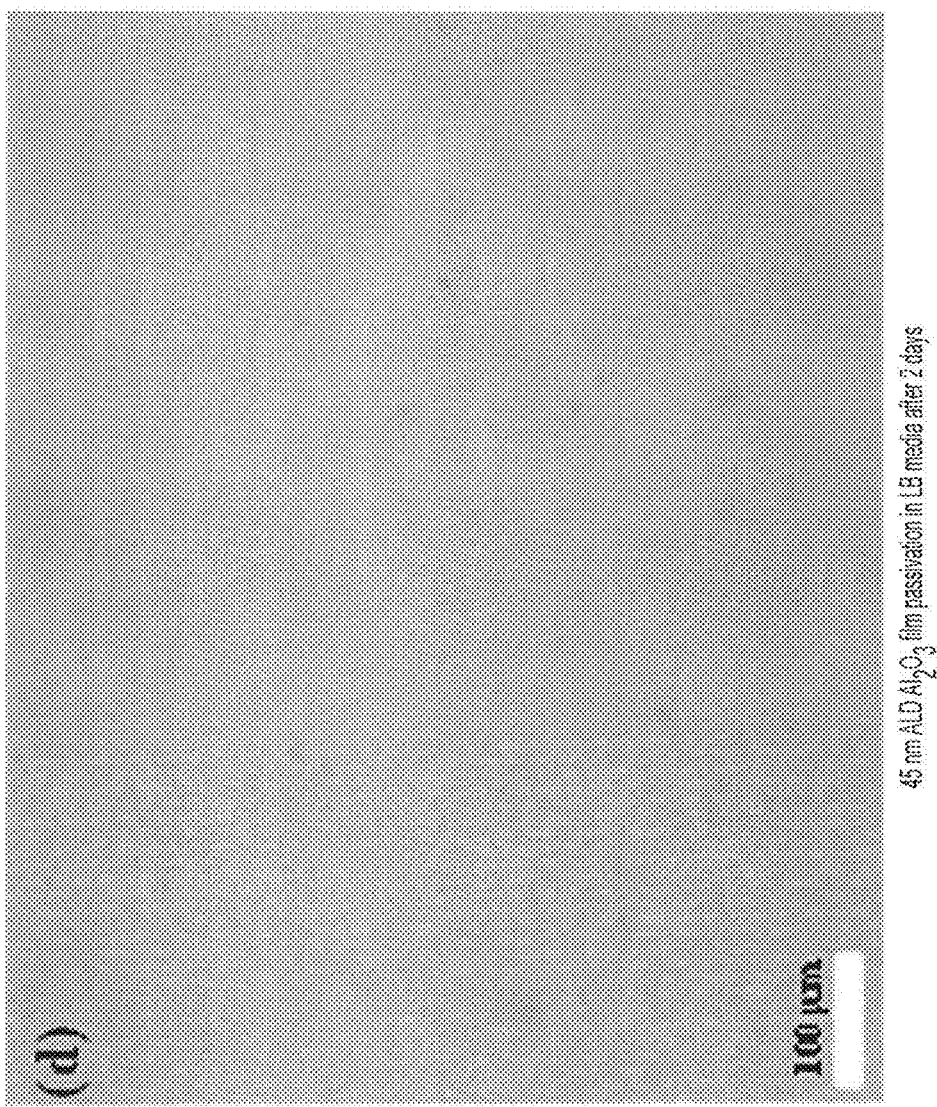
FIG. 12 is an optical microscopy image of another SAW biofilm sensor assembled in accordance with FIGS. 2-7E passivated by ALD of $Al_2O_3$ with a passivation layer thickness of 45 nm showing no damage.

More particularly, FIG. 9 is an optical microscopy image of a SAW biofilm sensor assembled in accordance with FIGS. 2-7E passivated by ALD of $Al_2O_3$ with a passivation layer thickness of 20 nm showing damaged areas. FIG. 10 is an optical microscopy image of another SAW biofilm sensor assembled in accordance with FIGS. 2-7E passivated by ALD of $Al_2O_3$ with a passivation layer thickness of 30 nm showing damaged areas. FIG. 11 is an optical microscopy image of yet another SAW biofilm sensor assembled in accordance with FIGS. 2-7E passivated by ALD of $Al_2O_3$ with a passivation layer thickness of 40 nm showing damaged areas. Finally, FIG. 12 is an optical microscopy image of another SAW biofilm sensor assembled in accordance with FIGS. 2-7E passivated by ALD of $Al_2O_3$ with a passivation layer thickness of 45 nm showing no damage.

Based on these experiments, the minimum required thickness of ALD $Al_2O_3$ film for the passivation of ZnO was 45 nm. Since thicker passivation films caused a high loss of sensitivity due to more initial mass loading, the 45 nm thick $Al_2O_3$ film was selected to passivate the SAW sensor.

Figure 14:
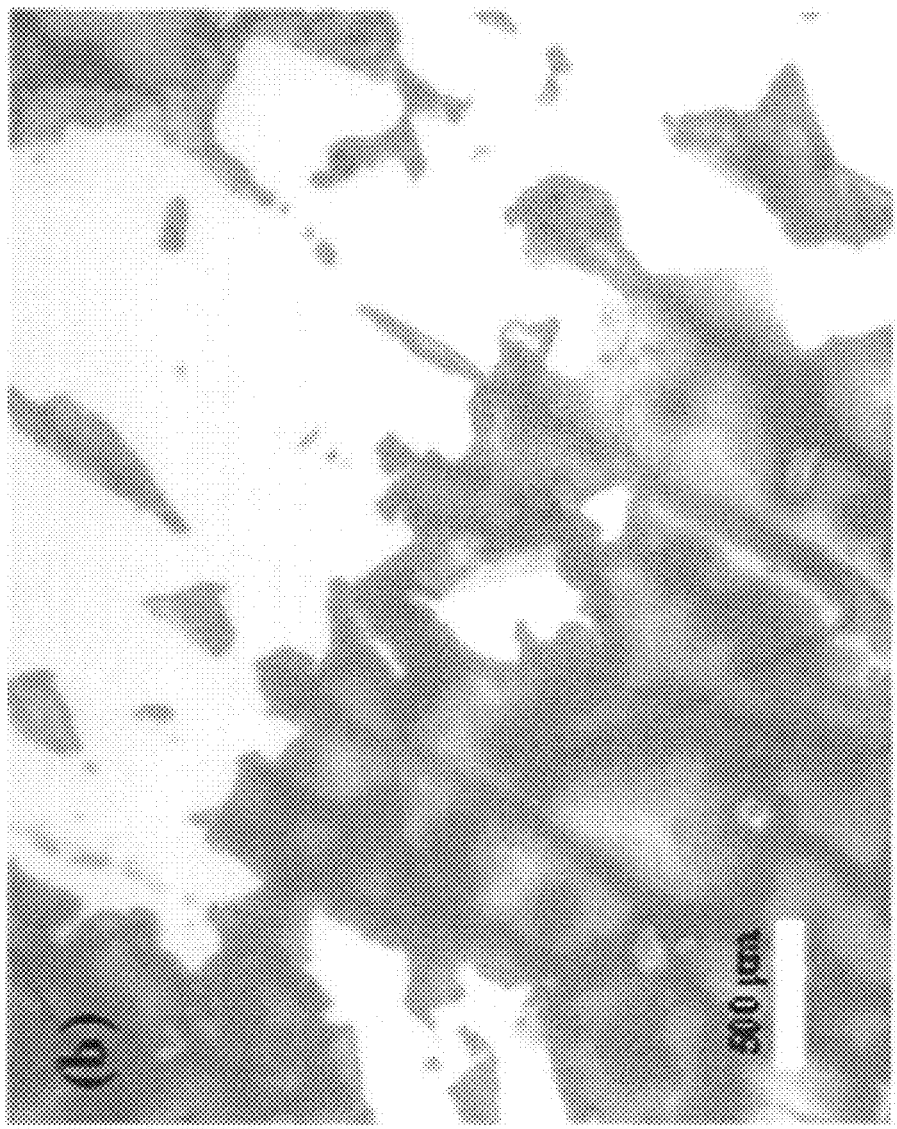
FIG. 14 is an optical surface image of another SAW biofilm sensor assembled in accordance with FIGS. 2-7E passivated by a 45 nm $Al_2O_3$ film using RF sputtering showing damage.
Figure 15:
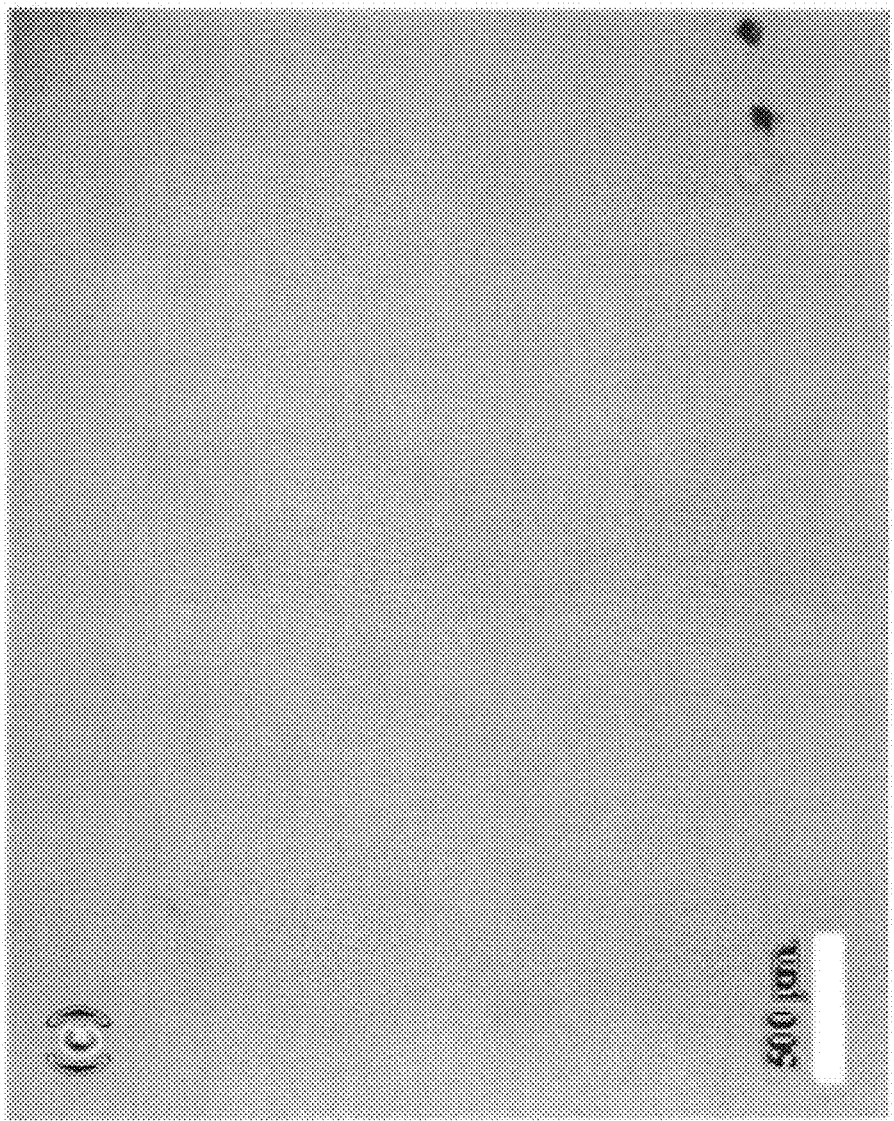
FIG. 15 is an optical surface image of another SAW biofilm sensor assembled in accordance with FIGS. 2-7E passivated by a 45 nm $Al_2O_3$ film using ALD showing no damage.

In addition to ALD, other $Al_2O_3$ film deposition methods were investigated in order to evaluate the dependence of passivation layer performance on the fabrication process. E-beam evaporation and RF-sputtering were used to deposit 45 nm of $Al_2O_3$ film. However, after two days in an LB media bacterial suspension, these two passivation films were not able to protect the ZnO layer as shown in FIGS. 13-15.

Figure 13:
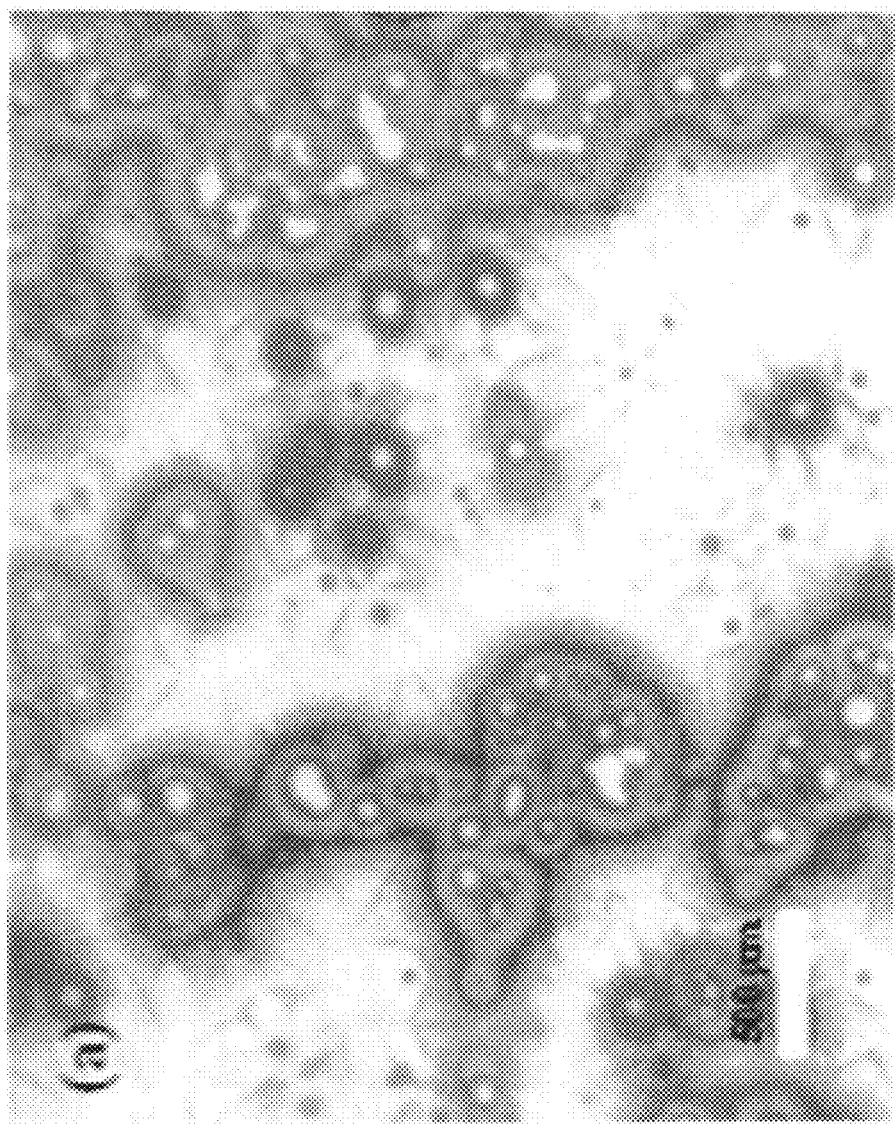
FIG. 13 is an optical surface image of another SAW biofilm sensor assembled in accordance with FIGS. 2-7E passivated by a 45 nm $Al_2O_3$ film using e-beam evaporation showing damage.

More particularly, FIG. 13 is an optical surface image of another SAW biofilm sensor 200 assembled in accordance with FIGS. 2-7E passivated by a 45 nm $Al_2O_3$ film using e-beam evaporation showing damage. FIG. 14 is an optical surface image of still another SAW biofilm sensor 200 assembled in accordance with FIGS. 2-7E passivated by a 45 nm $Al_2O_3$ film using RF sputtering showing damage. FIG. 15 is an optical surface image of yet another SAW biofilm sensor 200 assembled in accordance with FIGS. 2-7E passivated by a 45 nm $Al_2O_3$ film using ALD showing no damage.

This result can be due to non-uniform or lower density film deposition of IE-beam evaporation and RF-sputtering as compared to ALD. Therefore, ALD is a highly advantageous fabrication process for effective passivation of the ZnO using $Al_2O_3$.

Passivated SAW Sensor Characterization

The mass sensitivity and detection limit of the SAW sensor were studied by loading 10 μl of deionized (DI) water onto the sensor. A volume of 10 μl was used since that was the minimum volume of DI water required to cover the area between the two IDTs of the sensor. By measuring the resonant frequency shift upon mass loading, the sensitivity of the SAW sensor was calculated based on equations (3) and (6). The mass detection limit of the sensor was also calculated using the equipment resolution and the sensitivity.

Real-Time Resonant Frequency Monitoring

Figure 16:
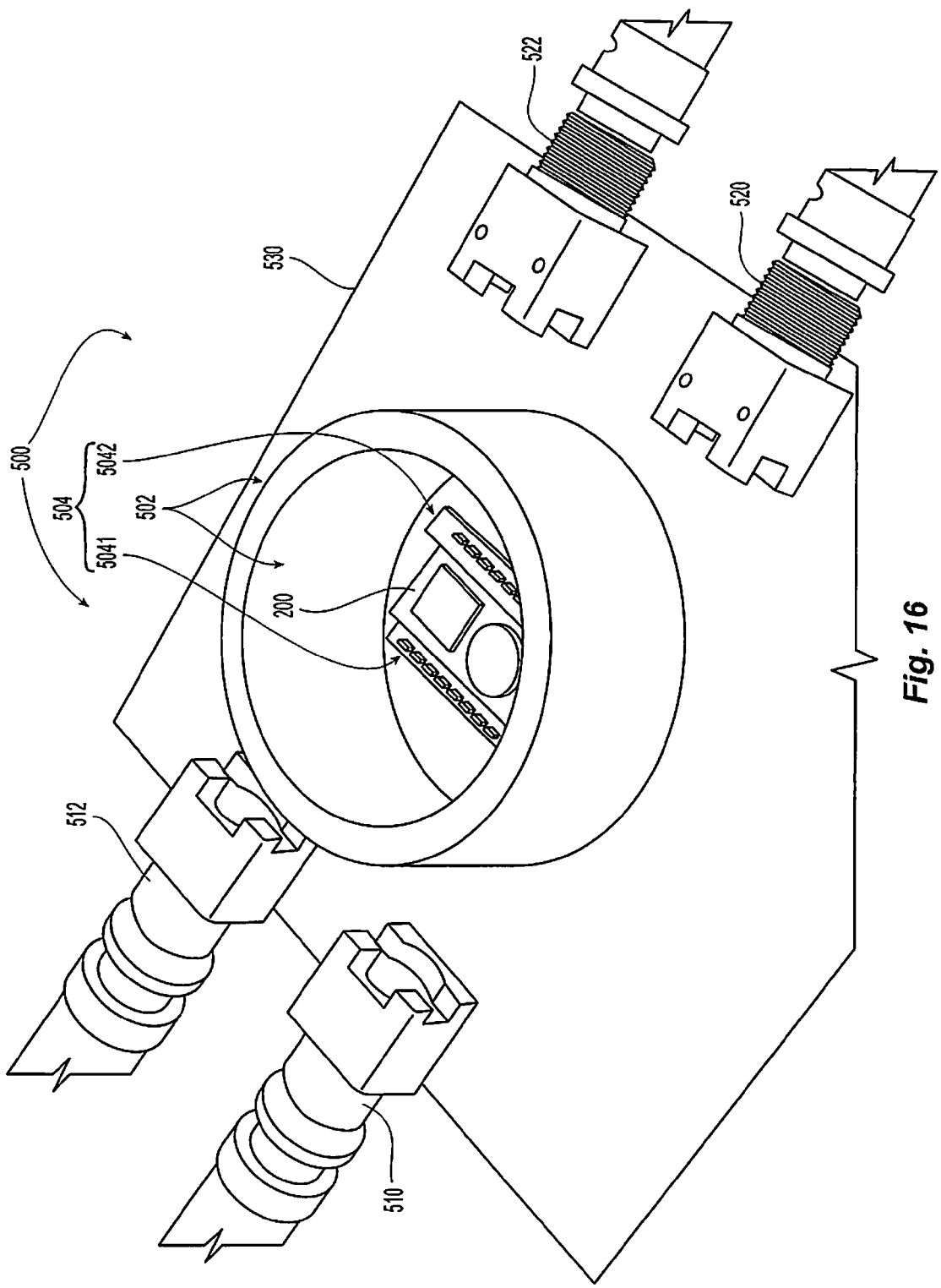
FIG. 16 is a top perspective view of a SAW biofilm sensor assembled in accordance with FIGS. 2-7E as a packaged unit together with other components for biofilm sensing according to one embodiment of the present disclosure.

As illustrated in FIG. 16, for real time resonant frequency monitoring in bacterial biofilm formation experiments, a custom biofilm sensing package 500 was designed to enable low impedance Bayonet Neill-Concelman (BNC) cable connections for RF applications with a network analyzer (HP8510B, Agilent Inc. USA) (not shown). The device biofilm sensing package 500 includes a bacterial growth well 502, which was used to prevent bacterial growth media leakage and localize the bacterial growth, and a chip package 504, that includes two separate portions 5041 and 5042 on either longitudinal side of the SAW sensor 200 connecting the sensor input BNC cable 510 and sensor output BNC cable 512 and BNC cables 520 and 522 for generating RF radiation. The SAW sensor 200 was placed in the bacterial growth well 502 and connected to the BNC connectors 520 and 522 by lead soldering on the chip package 504. The network analyzer was used to sweep a wide range of RF frequencies into the sensor 200 and the device resonant frequency was analyzed using S-parameter analysis. The resonant frequency of the sensor 200 was detected by measuring a low peak of the reflective power ratio ($S_{11}$) in the network analyzer. Data was collected and saved to a computer (not shown) every minute using general purpose interface bus (GPIB) communication (not shown) with the network analyzer.

Biofilm Growth Experiments with the SAW Sensor

*E. coli* W3110 was cultured in a shaking incubator for about 16 hours. The grown bacterial suspension was diluted with LB media or 10% FBS to make the initial $OD_{600}$ approximately 0.21-0.23. The total volume of the diluted bacterial suspension in the growth well 502 was 20 ml in experiments with both types of media. The FBS solution was prepared to a 10% concentration by diluting with Dulbecco/Vogt modified Eagle's minimal essential medium (Invitrogen Inc, USA). After filling the bacterial growth well 502 with the diluted bacterial suspension, the well was sealed by paraffin film to prevent evaporation of the media during the experiment. The package 500 was placed on a 37° C. hotplate 530, and a polystyrene container (not shown) covered the whole package to reduce the temperature gradient near the test setup. After each biofilm growth experiment, the sensor 200 was recalibrated using DI water loading. The thickness of biofilm was measured optically by the distance difference between the focal plane of the sensor surface and the focal plane of the top of any accumulated biofilm.

Results and Discussion

ZnO Film Characterization

The generation of Love mode SAW was confirmed by investigating the lattice orientation of the deposited ZnO thin film, X-ray diffraction (XRD) was employed for crystal structure characterization of the ZnO layer after PLD deposition on a $SiO_2$/Si substrate by measuring the diffraction angle (2θ). The diffraction angles of the in the ZnO film at 34.25° and 72.25°, corresponding to c-axis (002) and (004) lattice orientations, were the most intensive reflections in the PLD prepared ZnO film. This c-axis orientation of ZnO crystal lattice ((00L) direction) was perpendicular to the substrate so that the Love mode of SAW generation was dominant on the surface of the sensor [15-22].

Photoluminescence (PL) spectroscopy was used to investigate the crystal quality of the ZnO film. The peak wavelength of the emitted light was approximately 380 nm, corresponding to the characteristic ZnO bandgap energy (3.3 eV). Therefore, the PL spectroscopy result confirmed that the PLD-prepared ZnO film had a low number of impurities.

Biofilm Cleaning

Consecutive biofilm growth tests using the same device are essential to investigate the reliability and repeatable operation of the SAW sensor. To test the sensor over multiple biofilm growth experiments, surface cleaning after a biofilm growth experiment was crucial for subsequent biofilm growth; cleaning not only sterilized the sensor, but also prevented initial mass loading due to the uncleaned biofilm and the resulting significant loss of sensitivity. Oxygen plasma applied for 30 s at 150 W RF-power was successfully employed to clean any remaining biofilm as shown in FIGS. 17 and 18

Figure 17:
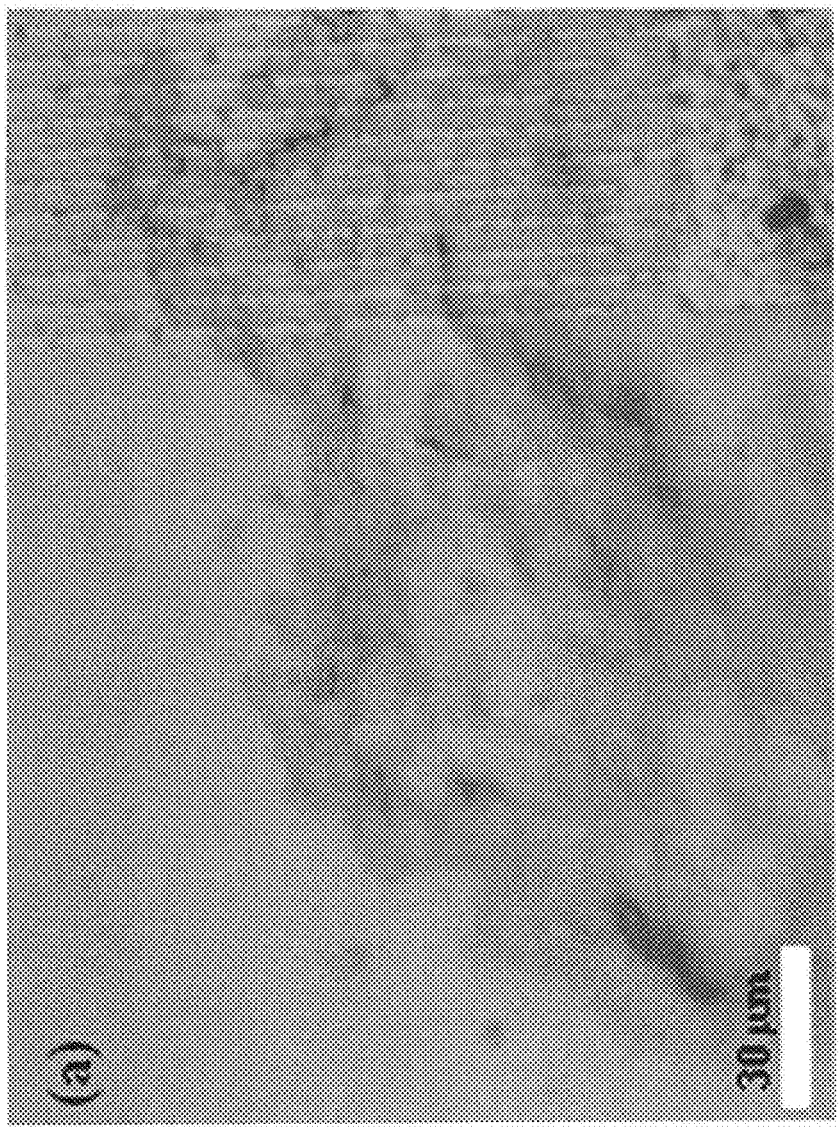
FIG. 17 is an optical microscopy image of the surface of a SAW biofilm sensor assembled in accordance with FIGS. 2-7E before biofilm cleaning.

FIG. 17 is an optical microscopy image of the surface of the SAW biofilm sensor 200 assembled in accordance with FIGS. 2-7E before biofilm cleaning.

Figure 18:
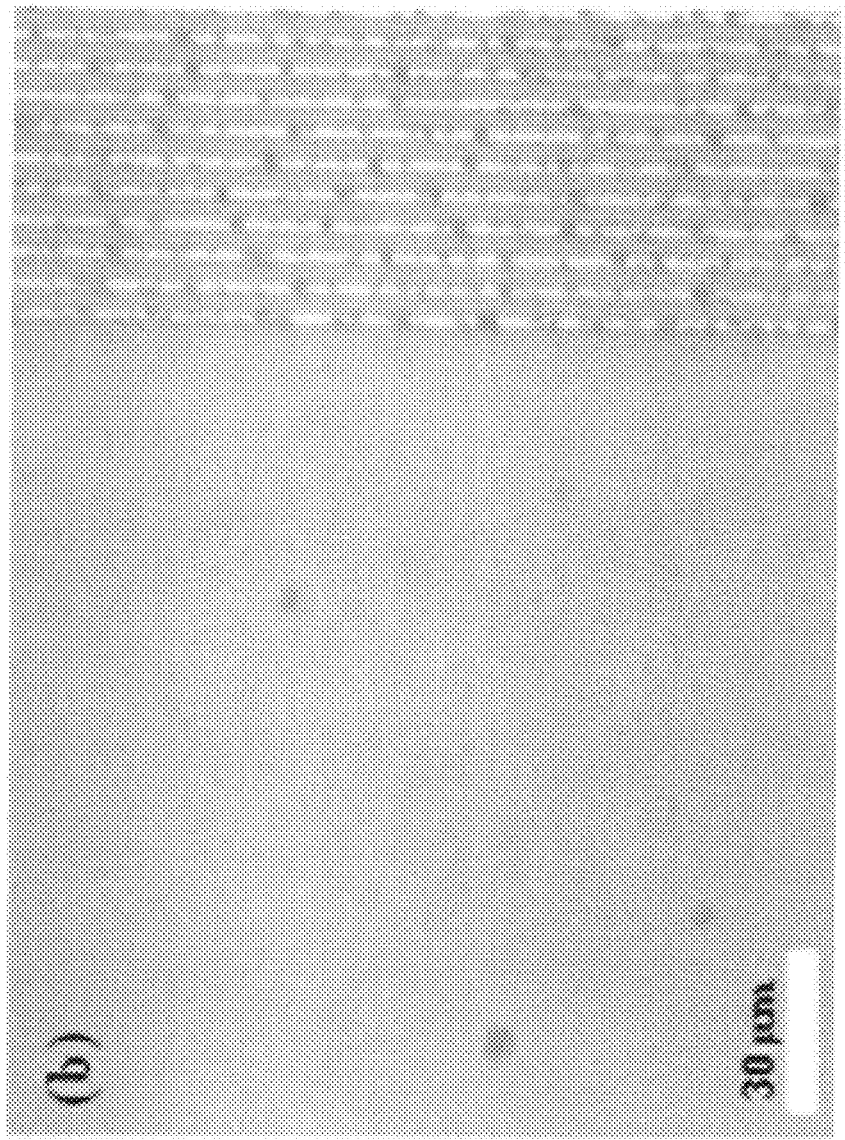
FIG. 18 is an optical microscopy image of the surface of the SAW biofilm sensor assembled in accordance with FIGS. 2-7E after oxygen plasma biofilm cleaning.

FIG. 18 is an optical microscopy image of the surface of the SAW biofilm sensor 200 assembled in accordance with FIGS. 2-7E after oxygen plasma biofilm cleaning.

The 45 nm ALD $Al_2O_3$ film passivation and oxygen plasma biofilm cleaning method enable SAW sensor 200 to be reusable over consecutive biofilm growth experiments.

Sensor Sensitivity

The sensitivity and detection limit of the SAW sensor were studied and calculated by loading 10 μl of DI water on the sensor and monitoring the magnitude of the resonant frequency shift. After loading 10 si of DI water, the resonant frequency shift of the SAW sensor was measured to be about 188 KHz by the network analyzer. Hence, the sensitivity of the sensor was $1.88 \times 10^{10}$ Hz/g. Based on the network analyzer resolution (0.1 Hz), the detection limit of the sensor (resolution/sensitivity) was approximately 5.3 pg (picograms). Since the mass of a bacterium is known to be approximately 1 pg [44], this detection limit validates the SAW sensor application for bacterial biofilm monitoring.

Biofilm Growth Experiments in the SAW Sensor

Figure 19:
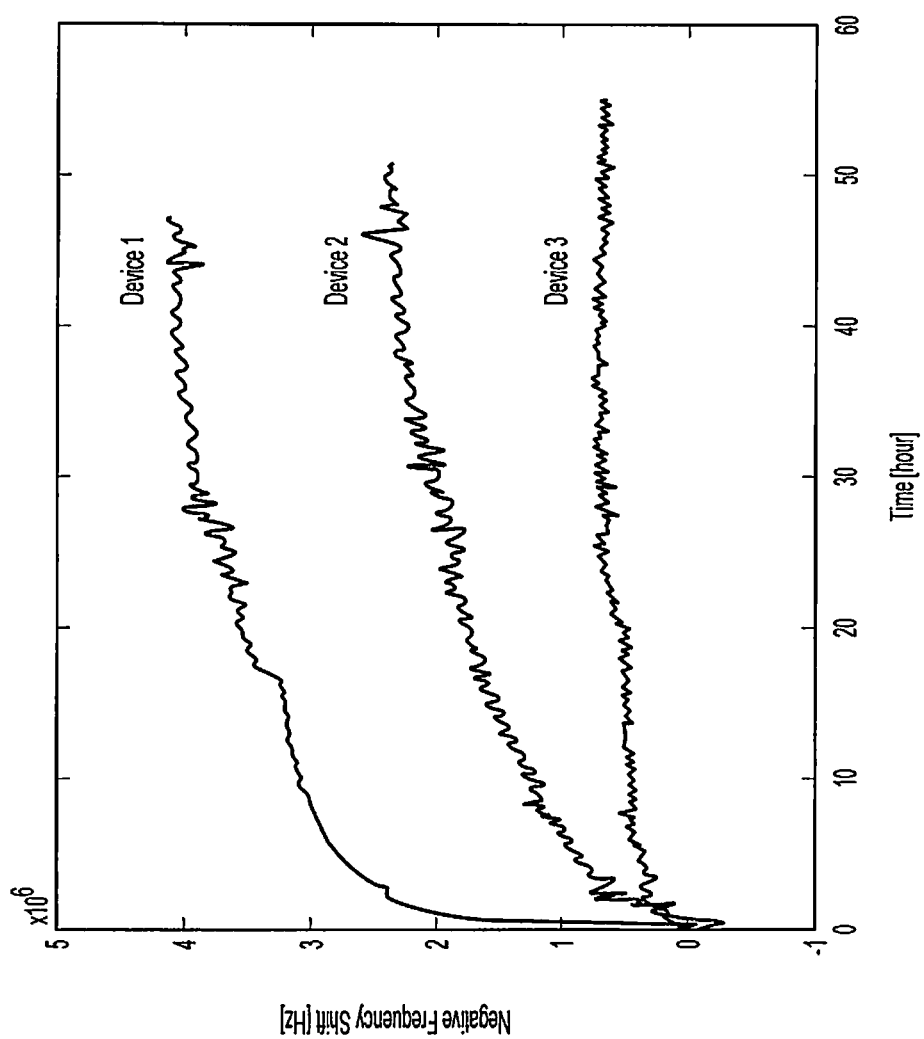
FIG. 19 is a graphical plot of negative resonant frequency shift results for SAW biofilm sensors assembled in accordance with FIGS. 2-7E versus time due to lysogeny broth (LB) biofilm growth for three newly fabricated SAW transducers.
Figure 20:
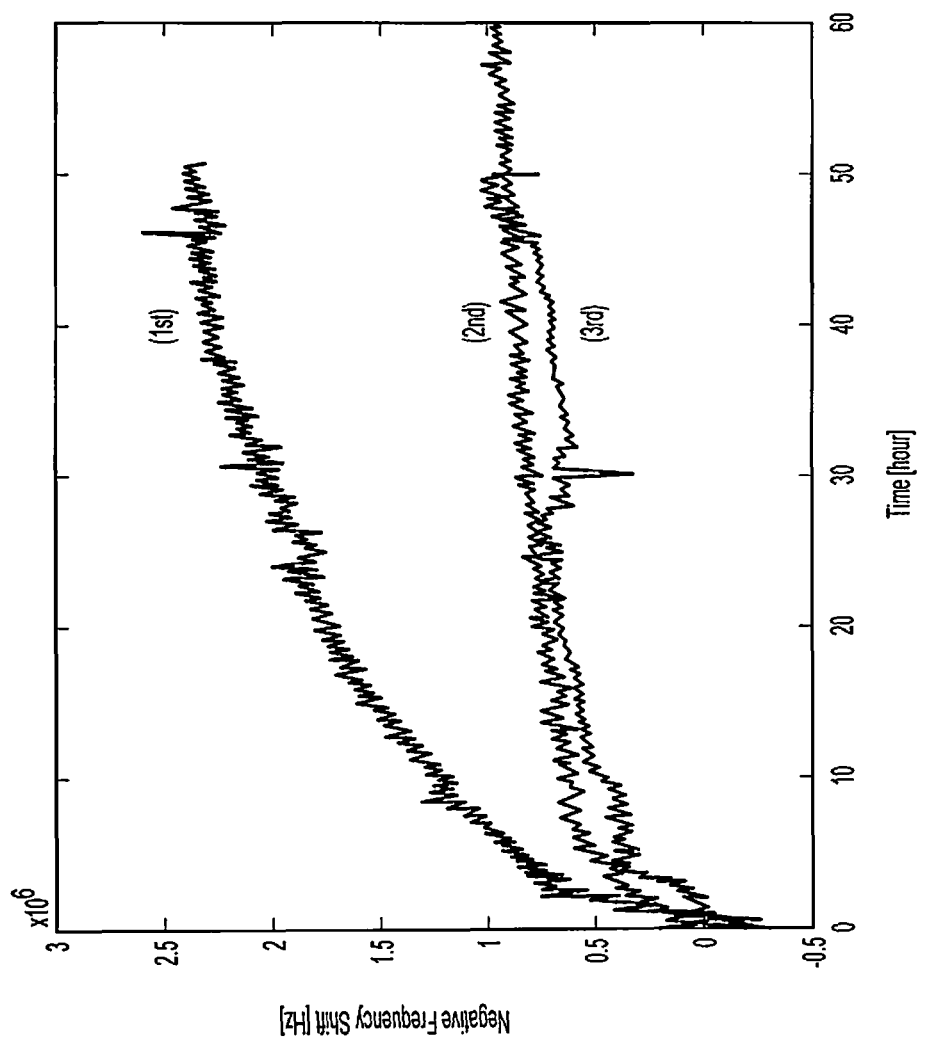
FIG. 20 is a graphical plot of negative resonant frequency shift results for a SAW biofilm sensor assembled in accordance with FIGS. 2-7E versus time due to lysogeny broth biofilm growth in three sequential growth experiments using one device in an LB.
Figure 21:
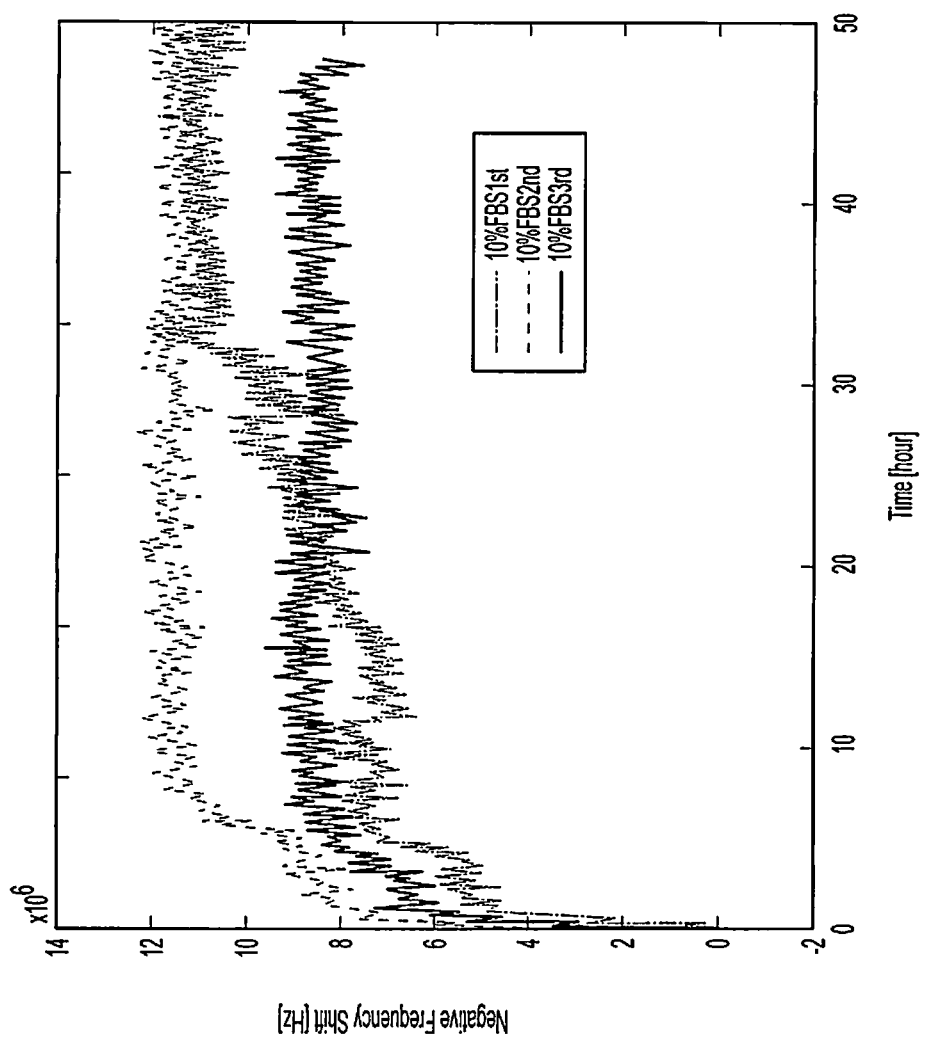
FIG. 21 is a graphical plot of negative resonant frequency shift results for a SAW biofilm sensor assembled in accordance with FIGS. 2-7E versus time in three growth experiments using a newly fabricated sensor in 10% fetal bovine serum (FBS)

The resonant frequency shift results of the SAW sensor due to the biofilm growth in LB media and in 10% PBS are shown in FIGS. 19, 20 and 21.

FIG. 19 is a graphical plot of negative resonant frequency shift results the SAW biofilm sensors assembled in accordance with FIGS. 2-7E versus time due to lysogeny broth (LB) biofilm growth for three newly fabricated SAW transducers.

FIG. 20 is a graphical plot of negative resonant frequency shift results for a SAW biofilm sensor assembled in accordance with FIGS. 2-7E versus time due to lysogeny broth biofilm growth in three sequential growth experiments using one device in an LB.

FIG. 21 is a graphical plot of negative resonant frequency shift results for a SAW biofilm sensor assembled in accordance with FIGS. 2-7E versus time in three growth experiments using a newly fabricated sensor in 10% fetal bovine serum (FBS).

In nature, bacterial growth in hatch culture begins with a lag phase where bacteria are not dividing but are actively adapting to the culture conditions. After this period, bacteria divide at a fast rate during the exponential phase of growth. Eventually, once the reactor contains a high population density and a limited supply of nutrients, the culture reaches stationary phase [45].

FIG. 19 shows the resonant frequency shift results from three newly fabricated devices (device 1, 2, and 3) in the first biofilm growth experiment in LB media. The frequency shift results of each new sensor show exponential resonant frequency changes at the beginning without the preceding lag phase as compared to the natural bacterial growth trend. These output responses of the SAW sensor can be because the overnight cultured *E. coli* are in a metabolically active state. When active bacteria are diluted to the same growth media, the lag phase may not be observed because bacteria do not have to change their metabolism [46]. However, the stationary phase frequency shifts in LB media biofilm experiments are varied, i.e. 0.8 MHz, 2.3 MHz, and 4.1 MHz for each device.

FIG. 20 illustrates the results when one of the newly fabricated SAW sensors (device 2) after the first experiment of FIG. 19 was selected and used for two additional sequential biofilm growth experiments, i.e., (2nd) and (3rd) in LB media, compared to the biofilm growth experiment for Device 2 in FIG. 19, designated as (1st), with the oxygen plasma cleaning applied between uses. The frequency shift results of sequential biofilm growth experiments in LB media as shown in FIG.

20 correspond to an exponential growth at the beginning, but the frequency shift observed during stationary phase also varies from 1 MHz to 2.3 MHz. The detection limit of the SAW sensor after each sequential biofilm growth experiment was studied by loading 10 μl DI water on the sensor. The summary of the calculated detection limit of the SAW sensor for the consecutive experiments are shown in Table 1.

TABLE 1

Summary of the detection limit of the SAW sensor in sequential biofilm growth experiments.

| | Before biofilm experiment | After $1^{st}$ biofilm growth experiment | After $2^{nd}$ biofilm growth experiment | After $3^{rd}$ biofilm growth experiment |
|---|---|---|---|---|
| Frequency shift due to 10 μl DI water | 185 kHz | 157 kHz | 141 kHz | 143 kHz |
| Sensitivity | $1.85 \times 10^{10}$ Hz/g | $1.57 \times 10^{10}$ Hz/g | $1.41 \times 10^{10}$ Hz/g | $1.43 \times 10^{10}$ Hz/g |
| Detection limit | 5.4 pg | 6.4 pg | 7.1 pg | 7.0 pg |

As shown in Table 1, the detection limit of the sensor changed minimally after consecutive biofilm growth experiments, demonstrating excellent sensitivity recovery of the sensor. Therefore, the large variance in the final resonant frequency shift seen in LB media is not a result of sensor degradation, but can be due to non-uniform growth of the biofilm based on the results shown in FIGS. 19 and 20 and in Table 1. To investigate the biofilm growth variance in LB media and in 10% FBS, twelve test devices were prepared and placed in a bacterial suspension prepared as previously described. The biofilm thickness was measured after two days at 30 to 40 locations on the devices using an optical microscope.

Figure 22:
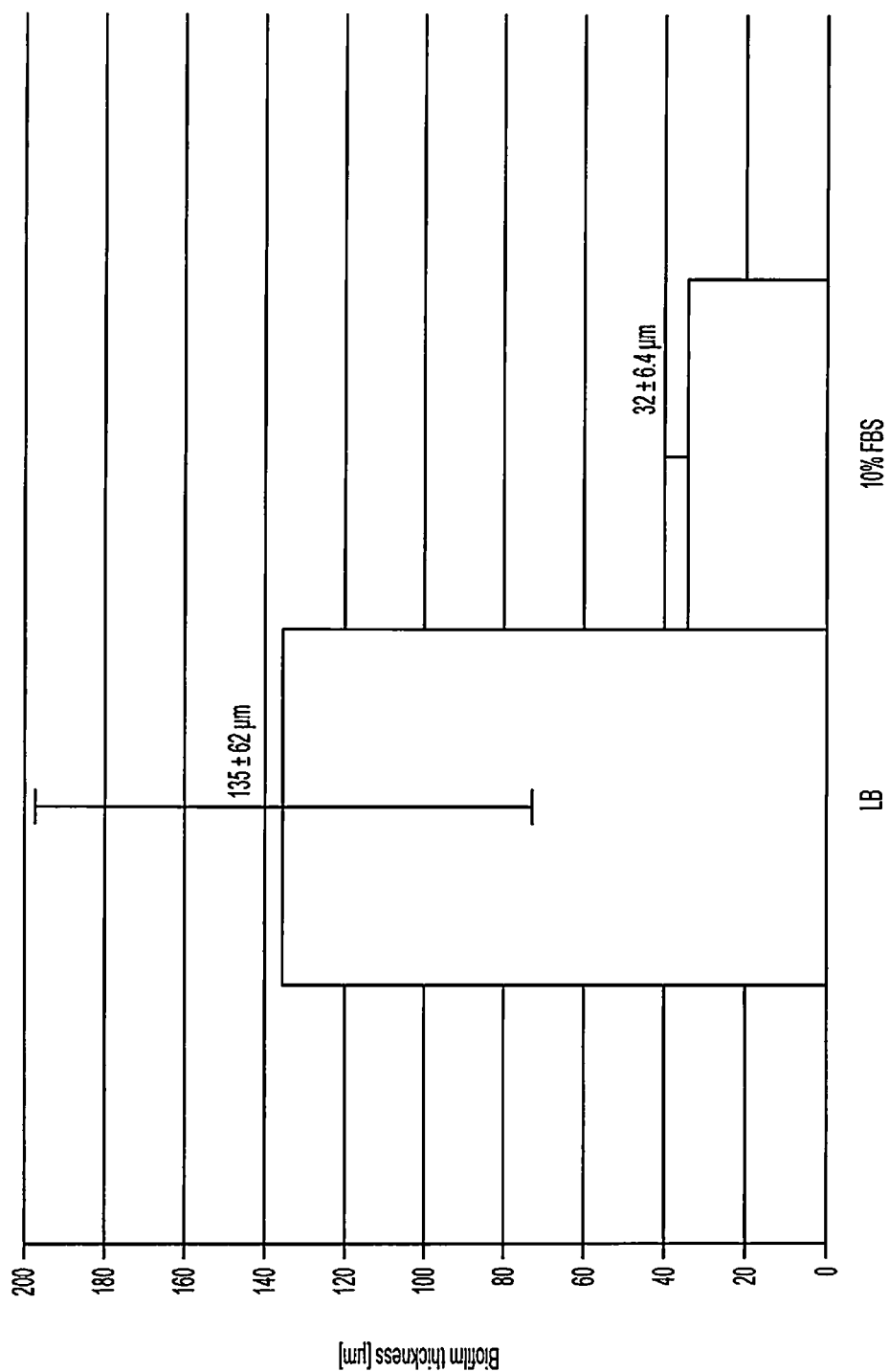
FIG. 22 is a graphical plot of averaged biofilm thickness and standard deviation in LB media and in 10% FBS over 30-40 locations measured by optical microscopy.

FIG. 22 is a graphical plot of averaged biofilm thickness and standard deviation in LB media and in 10% FBS over 30-40 locations measured by optical microscopy. As shown in FIG. 22, the measured average biofilm thicknesses in LB media and in 10% FBS were 135 μm and 32 μm respectively.

The standard deviation of the measured biofilm thickness in LB media (62 μm, about 46% of the average biofilm thickness) was significantly more than the standard deviation in 10% FBS (6.4 μm, about 20% of average biofilm thickness).

These results correspond to the large growth variance in LB media measured by the resonant frequency shift of the SAW sensor. Based on these experimental biofilm growth variance results and the sensitivity characterization work as shown in Table 1, the stationary phase resonant frequency shift variation in LB media in FIGS. 19 and 20 can be attributed to the natural variation in biofilm growth. The LB media, which is a standard bacterial growth media, is composed of essential materials for *E. coli* growth, such as amino acids, yeast, and NaCl. Thus, the media can provide a favorable environment for biofilm growth. The 10% FBS is mainly composed of diverse blood proteins, such as globular protein and Bovine Serum Albumin (BSA), and has been widely used as a simulated in vivo condition for mammalian cell culture. These composition differences between in LB media and in 10% FBS will cause different bacterial growth rates in each media, contributing to the observed difference in biofilm thickness.

FIG. 21 illustrates the resonant frequency shift results in 10% FBS biofilm growth experiments. In 10% FBS tests, a newly fabricated SAW sensor was used in three consecutive bacterial biofilm growth experiments, using oxygen plasma cleaning between experiments. As shown in FIG. 21, the frequency shift of the sensor also corresponds to exponential growth trend. Furthermore, the variation in the stationary phase in each experiment was only about 0.3 MHz which was much less than variation in LB media (about 3.3 MHz). This smaller difference in the final frequency shifts in 10% FBS compared to the LB media biofilm growth experiments can be due to the more uniform biofilm growth in 10% FBS as shown in FIG. 22.

Figure 23:
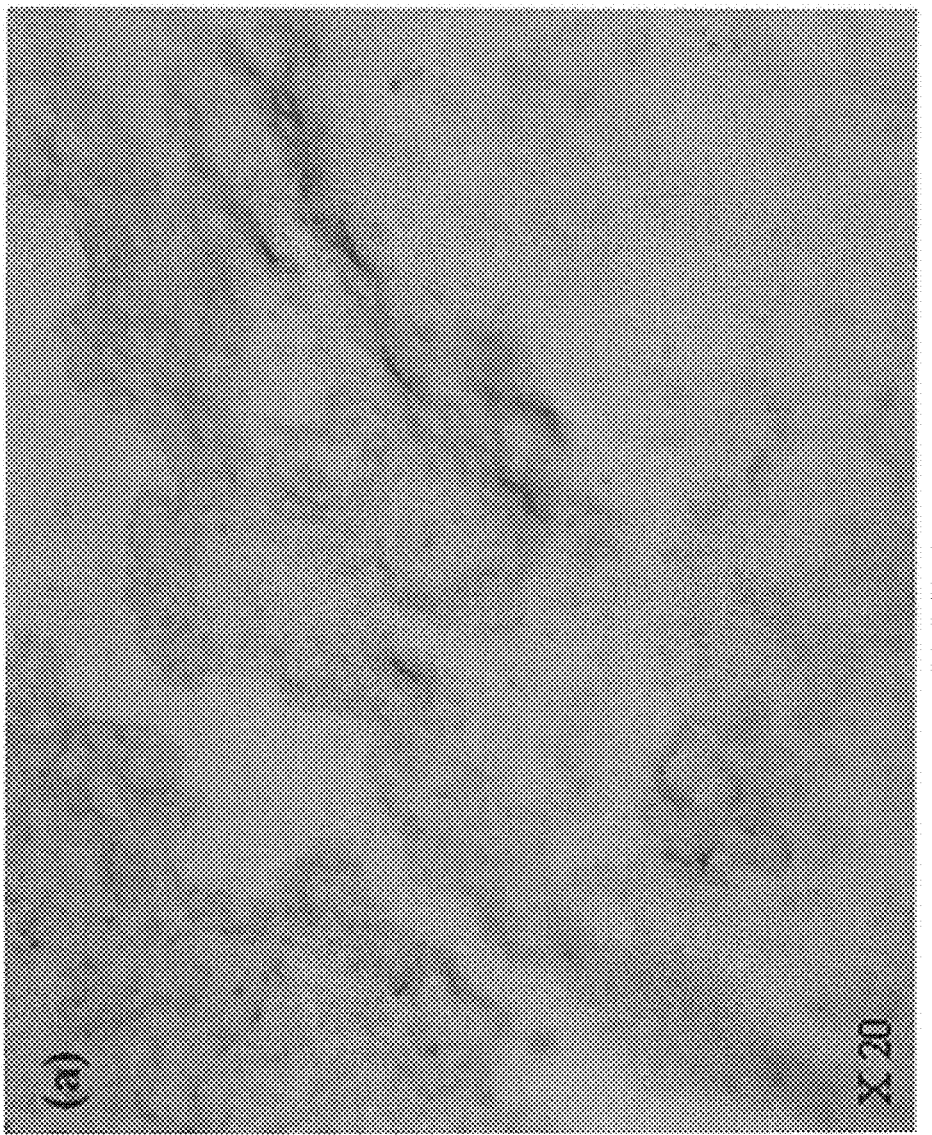
FIG. 23 is a microscopy image of a SAW biofilm sensor assembled in accordance with FIGS. 2-7E after biofilm growth experiments in LB media.
Figure 24:
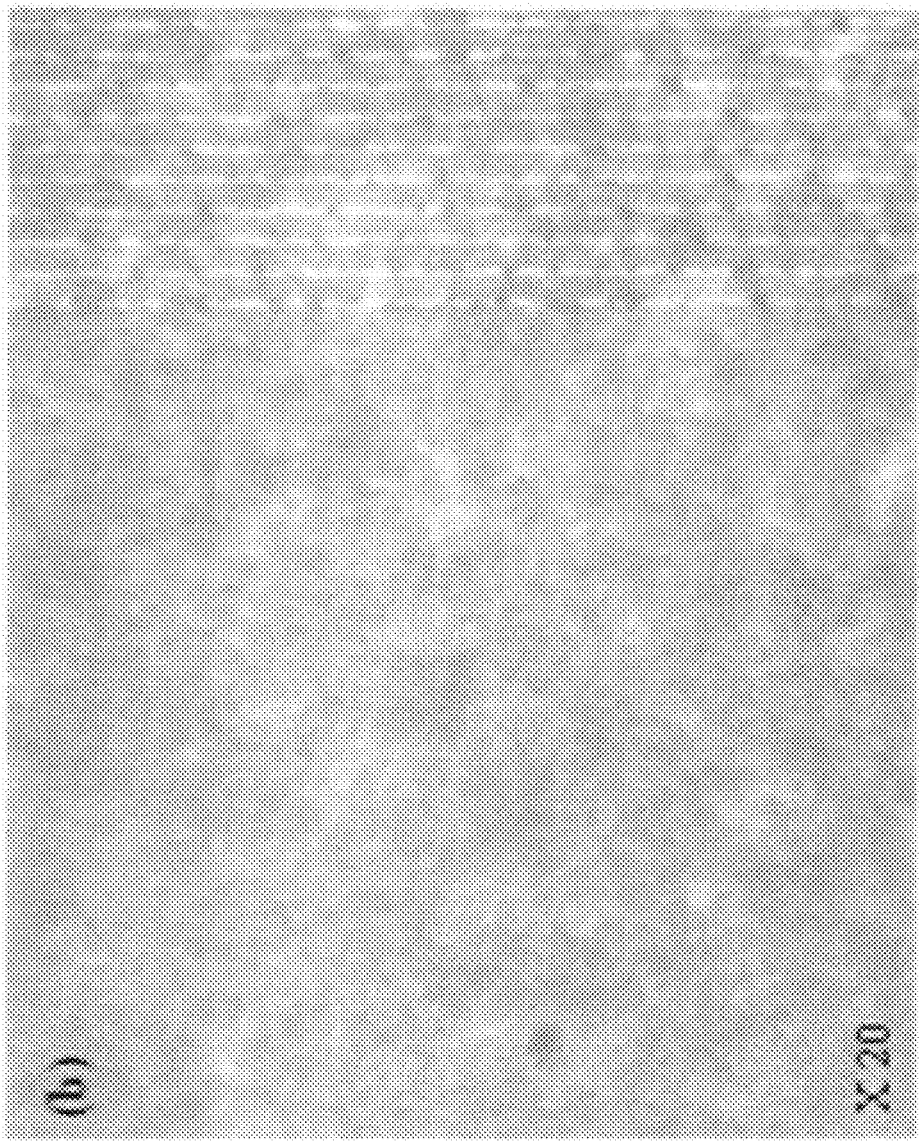
FIG. 24 is a microscopy image of the SAW biofilm sensor of FIG. 23 assembled in accordance with FIGS. 2-7E after biofilm growth experiments in 10% FBS.

FIG. 23 is a microscopy image of a SAW biofilm sensor assembled in accordance with FIGS. 2-7E after biofilm growth experiments in LB media;

FIG. 24 is a microscopy image of the SAW biofilm sensor of FIG. 23 assembled in accordance with FIGS. 2-7F, after biofilm growth experiments in 10% FBS;

After biofilm growth experiments in each media, the presence of bacterial biofilm on the SAW sensor was confirmed by optical microscopy as shown images in FIGS. 23 and 24.

As shown by the data, the 45 nm ALD $Al_2O_3$ passivated SAW sensor was able to measure biofilm growth repeatably using oxygen plasma cleaning between experiments. The final frequency shift results in LB media were more variable than those in 10% FBS since the composition of the LB media was a more favorable environment to *E. coli*, thereby indicating non-uniform biofilm growth in each experiment [47]. The observed SAW sensor outputs in both media followed the same growth trends. Moreover, the 10% FBS results suggest that the SAW sensor can be applied to in vivo biofilm detection in the future. Since the FBS is composed of blood proteins and plasma, the serum can be used to mimic an in vivo environment. The resonant frequency shift results of the SAW sensor in 10% HIS are more repeatable than results in LB media, rendering reliable operation of the sensor in an in vivo environment more likely. The effective passivation of the sensor using an ALD $Al_2O_3$ film also contributed to reliable sensing in 10% FBS.

Figure 25:
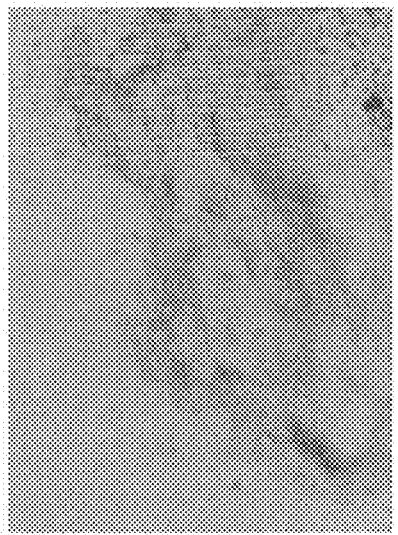
FIG. 25 is a microscopy image of a SAW biofilm sensor assembled in accordance with FIGS. 2-7E after cleaning with deionized water.

FIG. 25 is a microscopy image of a SAW biofilm sensor, such as SAW biofilm sensor 200 assembled in accordance with FIGS. 2-7E after cleaning with deionized water.

Figure 26:
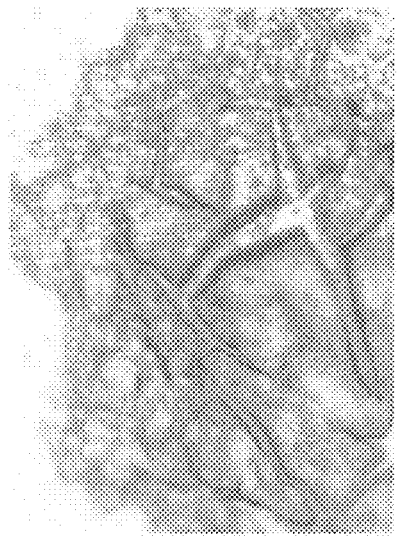
FIG. 26 is a microscopy image of the SAW biofilm sensor of RIG, 25 after ultrasonication cleaning in acetone for 3 hours.

FIG. 26 is a microscopy image of the SAW biofilm sensor of FIG. 25 after ultrasonication cleaning in acetone for 3 hours.

Figure 27:
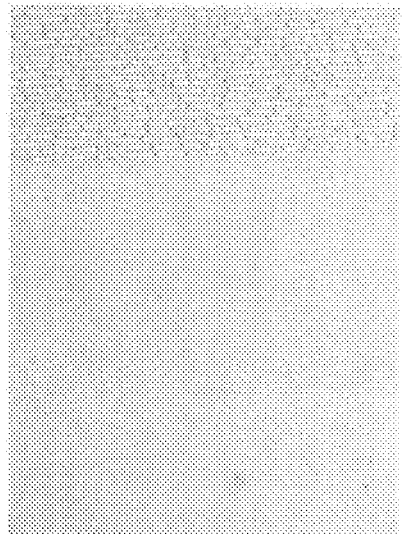
FIG. 27 is a microscopy image of the SAW biofilm sensor of FIGS. 25 and 26 after oxygen plasma cleaning for 30 seconds.

FIG. 27 is a microscopy image of the SAW biofilm sensor of FIGS. 25 and 26 after oxygen plasma cleaning for 30 seconds.

Figure 28:
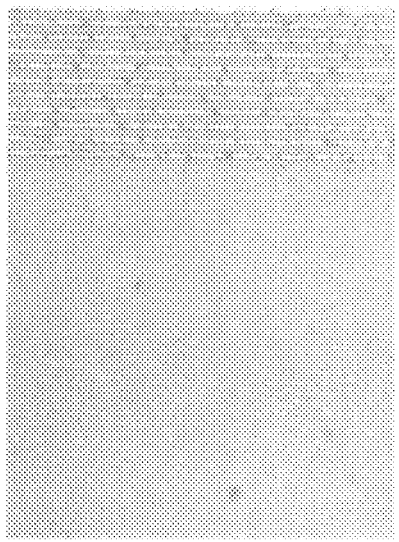
FIG. 28 is a microscopy image of the SAW biofilm sensor of FIGS. 25, 26 and 27 after a second biofilm growth experiment and oxygen plasma cleaning for 30 seconds.

FIG. 28 is a microscopy image of the SAW biofilm sensor of FIGS. 25, 26 and 27 after a second biofilm growth experiment and oxygen plasma cleaning for 30 seconds.

The results indicated by FIGS. 25 to 28 illustrate that the SAW sensor 200 can be reused after oxygen plasma cleaning, allowing for consecutive biofilm formation experiments using one sensor.

In view of the foregoing description, those skilled in the art will understand and appreciate that a novel ALD $Al_2O_3$ film passivated SAW sensor for real time biofilm monitoring has been successfully demonstrated. A high quality c-axis oriented ZnO film was deposited by PLD, and the sensor was effectively passivated by 45 nm of $Al_2O_3$ film using ALD to prevent ZnO damage in the bacterial growth media and animal serum. For the reliable passivation of the ZnO SAW sensor, ALD was an important fabrication method based on its highly dense and conformal film deposition capabilities. The SAW sensor can be reused after oxygen plasma cleaning, allowing for consecutive biofilm formation experiments using one sensor. The detection limit of the SAW sensor was approximately 5.3 pg. The resonant frequency shift results of the SAW sensor followed natural bacterial biofilm growth properties not only in LB media which provided a favorable bacterial growth environment, but also in 10% FBS as a simulated in vivo environment. These results validate the application of the SAW sensor for real-time bacterial growth monitoring.

Figure 29:
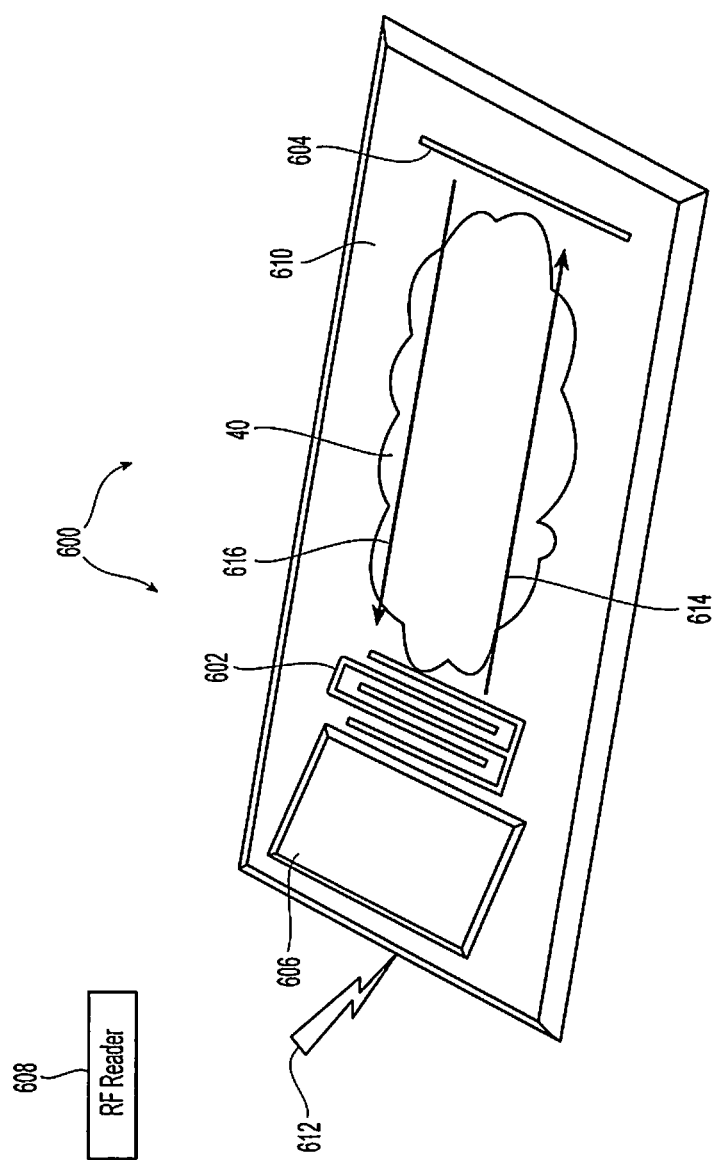
FIG. 29 is a perspective view a top perspective view of an exemplary embodiment of a SAW biofilm sensor that includes an antenna for radiofrequency (RF) coupling to a radiofrequency identification (RFID) reader.

FIG. 29 is a perspective view a top perspective view of an exemplary embodiment of a SAW biofilm sensor 600 disposed on a substrate 610. The SAW biofilm sensor 600 includes an IDT 602 and an RF reflective tag 604 each disposed on the substrate 610 on an opposite side of a biofilm 40 such that a transmitted SAW 614 originating from the IDT 602 is reflected by the reflective tag 604 as a reflected SAW 616 back to the IDT 602. The IDT 602 senses the reflected SAW 616 and via an antenna 606 in RF coupling 612 to an RF reader 608 to enable remote biofilm growth detection.

This SAW sensor 600 combined with RF wireless communication techniques can be used to detect in vivo biofilm growth, which is the groundwork for developing an implantable sensor for early biofilm detection and prevention of major infections.

Although the present disclosure has been described in considerable detail with reference to certain preferred version thereof, other versions are possible and contemplated. Therefore, the spirit and scope of the appended claims should not be limited to the description of the preferred versions contained therein.

Any element in a claim that does not explicitly state "means for" performing a specified function or "step for" performing a specified function, is not to be interpreted as a "means" or "step" clause as specified in 35 U.S.C. §112, ¶6. In particular, the use of "step of" in the claims is not intended to invoke the provisions of 35 U.S.C. §112, ¶6.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The embodiments of the present disclosure may be implemented by means of hardware comprising several distinct elements, and/or by means of a suitably programmed processor. In the device claim enumerating several means, several of these means may be embodied by one and the same item of hardware. The mere fact that certain measures are recited in mutually different dependent claims does not indicate that a combination of these measures cannot be used to advantage.

REFERENCES

The entire contents and teachings of the following references are incorporated herein by reference.

These references are identified as source documents for the particular portion of the foregoing description by indication of the number or numbers in parentheses [1]-[47] corresponding to one or more of the references below.

[1] J. W. C, Philip S. Stewart, E. P. Greenberg, Bacterial Biofilms: A Common Cause of Persistent infections, SCIENCE, VOL 284, (1999), p. 1318-1322,

[2] Sutherland, I. W., Bacterial exopolysaccharides their nature and production, Surface Carbohydrates of the Prokaryotic Cell, London, Academic Press, (1977), p. 27-96.

[3] J. W. Costerton, Z. Lewandowski, D. E Caldwell, D. R. Corber, H. M. Lappin-Scott, Bacterial biofilms in nature and disease, Annu. Rev. Microbiol, 41, (1987), p. 435-506.

[4] Liju Yang, and Yanbin Li, Detection of viable *Salmonella* using microelectrode-based capacitance measurement coupled with immunomagnetic separation, J MICROBIOL METH, 64, (2006), p. 9-16.

[5] Ebrahim Ghafar-Zadeh, Mohamad Sawan, Vamsy P. Chodavarapu, and Tahereh Hosseini-Nia, Bacteria Growth Monitoring Through a Differential CMOS Capacitive Sensor, IEEE T BIO-MED ENG, VOL. 4, NO. 4, (2010), p. 232-238.

[6] X. Munoz-Berbel, N. Vigues, A. T. A. Jenkins, J. Mas, F. J. Munoz, Impedimetric approach for qualifying low bacteria concentrations based on the changes produced in the electrode-solution interface during the pre-attachment stage, Biosens. Bioelectron., 23, (2008), p. 1540-1546.

[7] E. Spiller, A. Scholl, R. Alexy, K. Kummerer, G. A. Urban, A sensitive microsystem as biosensor for cell growth monitoring and antibiotic testing, Sensor Actuat A, 130-131, (2006), p. 312-321.

[8] Ewa Heyduk, Tomasz Heyduk, Fluorescent homogeneous immunosensors for detecting pathogenic bacteria, Anal. Biochem., (2010), p. 396, 298-303.

[9] Benjamin J. Privett, Jae Ho Shin, and Mark H. Schoenfisch, Electrochemical Sensors, Anal. Chem., 82, (2010), p. 4723-4741.

[10] Michiel van Leeuwen, Erik E. Krommenhoek, Joseph J. Heijnen, Han Gardeniers, Luuk A. M. van der Wielen and Walter M. Van Gulik, Aerobic Batch Cultivation in Micro Bioreactor with integrated Electrochemical Sensor Array, Biotechnol, Prog., Vol. 26, No. 1, (2010), p. 293-300.

[11] G. L. Harding, J. Du, P. R. Dencher, D. Barnett, E. Howe, Love wave acoustic immunosensor operating in liquid, Sens. Actuat A, 61, (1997), p. 279-286.

[12] J. Du, G. L. Harding, J. A. Ogilvy, P. R. Dencher, M. Lake, A study of Love-wave acoustic sensors, Sens. Actuat. A, 56, (1996), p. 211-219.

[13] J. Du, G. L. Harding, A. F. Collings, P. R. Dencher, An experimental study of Love-wave acoustic sensors operating in liquids, Sens. Actuat. A, 60, (1997), p. 54-61.

[14] K. Z. Kourosh, W. Wlodarskia, Y. Y. Chene, B. N. Frye, K. Galatsisa, Novel Love mode surface acoustic wave based immunosensors, Sens. Actuat B, 91, (2003), p. 143-147.

[15] S. Krishnamoorthy, A. A. Iliadis, Properties of high sensitivity ZnO surface acoustic wave sensors on $SiO_2$/(100) Si substrates, Solid-State Electron., 52, (2008), p. 1710-1716.

[16] H. Morkoc and U. Ozgur, Zinc Oxide: Fundamentals, Materials, and Device Technology (Chapter 1: General Properties of ZnO), WILEY-VCH Verag GmbH, Weinheim, 2009.

[17] R. D. Vispute et al., High quality crystalline ZnO buffer layers on sapphire (001) by pulsed laser deposition for III-V nitrides, Appl. Phys. Lett. 70 (20), (1997), p. 2735-2737.

[18] S. Krishnamoorthy, A. A. Iliadis, Development of high frequency ZnO/SiO2/Si Love mode surface acoustic wave devices, Solid-State Electron., 50, (2006), p. 1113-1118.

[19] S. Krishnamoorthy, A. A. Iliadis, Thaleia Bei, George P. Chrousos, An interleukin-6 ZnO/SiO2/Si surface acoustic wave biosensor, BIOSENS BIOELECTRON, 24, (2008), p. 313-318.

[20] M. C. Horrillo et al., Optimization of SAW sensors with a structure ZnO—SiO2-Si to detect volatile organic compounds, Sens. Actuat. B, 118, (2006), p. 356361, 2006.

[21] X. Chen, D. Liu, Temperature stability of ZnO-based Love wave biosensor with SiO2 buffer layer, Sens. Actuat. A, 156, (2009), p. 317-322.

[22] X. Chen, D. Liu, J. Chen, G. Wang, The effect of a SiO2 layer on the performance of a ZnO-based SAW device for high sensitivity biosensor applications, Smart Mater. Struct. 18, (2009), 115021.

[23] A. Springer, R. Weigel, A. Pohl, F. Seifert, Wireless identification and sensing using surface acoustic wave devices, IEEE ASME Trans Mechatron, 9, (1999), p. 745-756.

[24] Alfred Pohl, A Review of Wireless SAW Sensors, IEEE Trans Ultrason Ferroelectr Freq Control, Vol. 47, No. 2, (2000), p. 317-332.

[25] Arruda David L, Wilson William C, Nguyen Crystal, Yao Qi W, Caiazzo Robert, Talpasanu Ilie, Microelectrical sensors as emerging platforms for protein biomaker detection in point-of-care diagnostic, Expert Rev. of Mol. Diagn., Vol. 9, No. 7, (2009), p. 749-755.

[26] M. Bisoffi, Detection of viral bioagents using a shear horizontal surface acoustic wave biosensor, BIOSENS BIOELECTRON, 23, (2008), pp. 1397-1403.

[27] Y. Q. Fu, J. K. Luo, X. Y. Du, A. J. Hewitt, Y. Li, G. H. Markx, Recent developments on ZnO films for acoustic wave bio-sensing and microfluidic applications: a review, SENSOR ACTUAT B-CHEM, 143, (2010), p. 606-619.

[28] Irie R F, Natural antibody in human serum to neoantigen in human cultured cells grown in fetal bovine serum, J. Natl Cancer Inst. 52(4), (1974), p. 1051-1058.

[29] Glen McHale, Generalized concept of shear horizontal acoustic plate mode and Love wave sensors, Meas. Sci Technol. 14, (2003), p. 1847-1853.

[30] Biljana A. Cavic, Gordon L. Hayward, and Michael Thompson, Acoustic waves and the study of biochemical macromolecules and cells at the sensor-liquid interface, Analyst, 124, (1999), p. 1405-1420

[31] Bill Drafts, Acoustic Wave Technology Sensors, IEEE T MICROW THEORY, Vol. 49, No. 4, (2001), p. 795-802.

[32] Federal Communications Commission, Title 47 C.F.R., Chapter I, Subchapter D, Part 95, Subpart I, paragraph 1209, "Permissible communications", 77 FR 55733, as amended through Sep. 11, 2012.

[33] Douglas H. Lowndes, D. B. Geohegan, A. A. Puretzky, D. P. Norton, C. M. Rouleau, Synthesis of Novel Thin-Film Materials by Pulsed Lase Deposition, Science, VOL 273, (1996), p. 898-903.

[34] Susan E. Voss and Jont B. Allen, Measurement of acoustic impedance and feflectance in the human ear canal, J. Acoust. Soc. Am, 95 (1), (1994), p. 372-384.

[35] B. Jakoby, M. J. Vellekoop, Properties of Love waves: application in sensors, Smart Mater. Struct. 6, (1997), p. 668-679.

[36] J. Su, Z. B. Kuang, H. Liu, Love wave in ZnO/SiO2/Si structure with initial stresses, Journal of Sound and Vibration, 286, (2005), p. 981-999.

[37] R. C. Chang, S. Y. Chu, C. S. Hong, Y. T. Chuang, A study of Love wave devices in ZnO/Quartz and ZnO/LitaO3 structures, Thin Solid Films, 498, (2006), 146-151.

[38] W. C. Shih, H. Y. Su, M. S. Wu, Deposition of ZnO thin films on SiO2/Si substrate with Al2O3 buffer layer by radio frequency magnetron sputtering for high frequency surface acoustic wave devices, Thin Solid Films, 517, (2009), p. 3378-3381.

[39] W. C. Shih, T. L. Wang L. L. Hsu, Surface acoustic wave properties of aluminum oxide films on lithium niobate, Thin Solid Films, 518, (2010), p. 7143-7146.

[40] J. Du, G. L. Harding, A multilayer structure for Love-mode acoustic sensors, Sens, Actuat A, 65, (1998), p. 152-159.

[41] NIST Property Data Summaries, http://www.ceramics.nist.gov/srd/summary/emodox00.htm

[42] http://www.lenntech.com/teflon.htm, http://www.cct-plastics.com/teflonall.html

[43] Hang-Ju Ko, Myung-Soo Han, Young-Sik Park, Yun-Sik Yu, Byoung-In Kim, Sang Sub Kim, Improvement of the quality of ZnO substrates by annealing, J of Cryst Growth, 269, (2004), p. 493-498.

[44] Davis, Dulbecco, Eisen, Ginsberg, *Bacterial Physiology: Microbiology, Second Edition*, Maryland: Harper and Row, (1973), p. 96-97.

[45] Jeffrey V. Straight and Doraiswami Ramkrishna, Modeling of Bacterial Growth under Multiply-Limiting Conditions, Experiments under Carbon- or/and Nitrogen-Limiting Conditions, Biotechnol. Prog. 10, (1994), p. 588-605.

[46] Augustin J. C. et al., Significance of Inoculum Size in the Lag Time of *Listeria monocytogenes*, APPL. ENVION. MICROBIOL. Vol. 66, (2000), p. 1706-1710.

[47] Mariana T Meyer, Varnika Roy, William E Bentley, and Reza Ghodssi, Development and validation of a microfluidic reactor for biofilm monitoring via optical methods, J. Micromech. Microeng., 21, (2011), 054023.

[48] Federal Communications Commission, Title 47 C.F.R., Chapter I, Subchapter D, Part 95, Subpart E, paragraph 627, "MedRadio transmitters in the 401-406 MHz band", as amended through 77 FR 4268, Jan. 27, 2012.

What is claimed is:

1. A method of passivating a surface acoustic wave sensor (SAW) using atomic layer deposition (ALD), comprising:
   depositing on a zinc oxide (ZnO) surface of a SAW sensor in an ALD reactor an aluminum oxide ($Al_2O_3$) film;
   introducing vaporized trimethylaluminum (TMA) $Al_2(CH_3)_3$ into the ALD reactor;
   forming a single layer of the TMA on the ZnO surface;
   purging the single layer of the TMA of unbound TMA vapor to become a purged single layer of the TMA; and
   introducing water vapor into the ALD reactor to create a single atomic layer of aluminum oxide deposition as a passivation layer of the SAW sensor.

2. The method according to claim 1, further comprising,
   prior to introducing vaporized trimethylaluminum (TMA) $Al_2(CH_3)_3$ into the ALD reactor,
   fabricating a liquid precursor of trimethylaluminum (TMA) $Al_2(CH_3)_3$.

3. The method according to claim 2, further comprising,
   prior to introducing vaporized trimethylaluminum (TMA) $Al_2(CH_3)_3$ into the ALD reactor and after fabricating a liquid precursor of trimethylaluminum (TMA) $Al_2(CH_3)_3$,
   converting the liquid precursor to a vapor.

4. The method according to claim 1, further comprising:
   maintaining temperature inside the ALD reactor at 150 degrees Celsius.

5. The method according to claim 1, wherein the creating a single atomic layer of aluminum oxide deposition as a passivation layer of the SAW sensor occurs at a deposition cycle rate of 0.09 nanometers per cycle.

6. The method according to claim 1, further comprising:
depositing a layer of zinc oxide ZnO to provide the ZnO surface on the SAW sensor.

7. The method according to claim 6, wherein the depositing of a layer of zinc oxide ZnO as the surface as the ZnO surface on the SAW sensor includes depositing the layer of zinc oxide ZnO having a thickness of at least 40 nanometers (nm).

8. The method according to claim 6, wherein the depositing of a layer of zinc oxide ZnO as the surface as the ZnO surface on the SAW sensor includes depositing the layer of zinc oxide ZnO having a thickness of at least 45 nanometers (nm).

9. The method according to claim 1, wherein the passivation layer of the SAW sensor is deposited on a SAW transducer electrode pattern of the SAW sensor.

10. A system for passivating a surface acoustic wave sensor (SAW) using atomic layer deposition (ALD), comprising:
an atomic layer deposition (ALD) reactor configured to receive a SAW sensor, the SAW sensor including as a piezoelectric layer a zinc oxide (ZnO) surface,
the system at least configured to execute one or more actions to, or at least configured to enable a user to:
deposit on the zinc oxide (ZnO) surface of the SAW sensor received in the ALD reactor an aluminum oxide ($Al_2O_3$) film;
introduce vaporized trimethylaluminum (TMA) $Al_2(CH_3)_3$ into the ALD reactor;
form a single layer of the TMA on the ZnO surface;
purge the single layer of the TMA of unbound TMA vapor to become a purged single layer of the TMA; and
introduce water vapor into the ALD reactor to create a single atomic layer of aluminum oxide deposition as a passivation film layer of the SAW sensor.

11. The system according to claim 10, wherein the system is configured to execute one or more actions to, or is configured to enable a user to:
prior to introducing vaporized trimethylaluminum (TMA) $Al_2(CH_3)_3$ into the ALD reactor,
fabricate a liquid precursor of trimethylaluminum (TMA) $Al_2(CH_3)_3$.

12. The system according to claim 11, wherein the system is configured to execute one or more actions to, or is configured to enable a user to:
prior to introducing vaporized trimethylaluminum (TMA) $Al_2(CH_3)_3$ into the ALD reactor and after fabricating a liquid precursor of trimethylaluminum (TMA) $Al_2(CH_3)_3$,
convert the liquid precursor to a vapor.

13. The system according to claim 10, wherein the system is configured to execute one or more actions to, or is configured to enable a user to:
maintain temperature inside the ALD reactor at 150 degrees Celsius.

14. The system according to claim 10, wherein the system is configured to execute one or more actions such that, or is configured to enable a user such that:
the creating of a single atomic layer of aluminum oxide deposition as a passivation film layer of the SAW sensor occurs at a deposition cycle rate of 0.09 nanometers per cycle.

15. The system according to claim 10, wherein the system is configured to execute one or more actions to, or is configured to enable a user to:
deposit a layer of zinc oxide ZnO as the ZnO surface on the SAW sensor.

16. The system according to claim 15, wherein the system is configured to execute one or more actions such that, or is configured to enable a user such that, the depositing of a layer of zinc oxide ZnO as the surface as the ZnO surface on the SAW sensor includes depositing the layer of zinc oxide ZnO having a thickness of at least 40 nanometers (nm).

17. The system according to claim 15, wherein the system is configured to execute one or more actions such that, or is configured to enable a user such that, the depositing of a layer of zinc oxide ZnO as the surface as the ZnO surface on the SAW sensor includes depositing the layer of zinc oxide ZnO having a thickness of at least 45 nanometers (nm).

18. The system according to claim 10, wherein the system is configured to execute one or more actions such that, or is configured to enable a user such that, the passivation film layer of the SAW sensor is deposited on a SAW transducer electrode pattern of the SAW sensor.

19. A surface acoustic wave (SAW) biofilm sensor comprising:
a SAW transducer;
a piezoelectric film layer; and
a passivation film layer,
the piezoelectric film layer mounted over the SAW transducer and the passivation film layer mounted over the piezoelectric film layer,
the SAW biofilm sensor manufactured by a method of using atomic layer deposition (ALD), comprising:
depositing on a zinc oxide (ZnO) surface of the SAW biofilm sensor in an ALD reactor an aluminum oxide ($Al_2O_3$) film;
introducing vaporized trimethylaluminum (TMA) $Al_2(CH_3)_3$ into the ALD reactor;
forming a single layer of the TMA on the ZnO surface;
purging the single layer of the TMA of unbound TMA vapor to become a purged single layer of the TMA; and
introducing water vapor into the ALD reactor to create a single atomic layer of aluminum oxide deposition as the passivation layer of the SAW biofilm sensor.

20. The SAW biofilm sensor according to claim 19, wherein the method of using atomic layer deposition (ALD) further comprises:
prior to introducing vaporized trimethylaluminum (TMA) $Al_2(CH_3)_3$ into the ALD reactor,
fabricating a liquid precursor of trimethylaluminum (TMA) $Al_2(CH_3)_3$.

21. The SAW biofilm sensor according to claim 20, wherein the method of using atomic layer deposition (ALD) further comprises:
prior to introducing vaporized trimethylaluminum (TMA) $Al_2(CH_3)_3$ into the ALD reactor and after fabricating a liquid precursor of trimethylaluminum (TMA) $Al_2(CH_3)_3$,
converting the liquid precursor to a vapor.

22. The SAW biofilm sensor according to claim 19, wherein the method of using atomic layer deposition (ALD) includes wherein the
depositing on a zinc oxide (ZnO) surface of the SAW biofilm sensor in an ALD reactor an aluminum oxide ($Al_2O_3$) film includes the zinc oxide (ZnO) surface of the SAW biofilm sensor being a zinc oxide (ZnO) surface of a zinc oxide (ZnO) piezoelectric film layer that is the piezoelectric film layer of the SAW biofilm sensor.

23. The SAW biofilm sensor according to claim 19, wherein the method of using atomic layer deposition (ALD) includes wherein the depositing of a layer of zinc oxide ZnO as the surface as the ZnO surface on the SAW sensor includes depositing the layer of zinc oxide ZnO having a thickness of at least 40 nanometers (nm).

24. The SAW biofilm sensor according to claim 19, wherein the method of using atomic layer deposition (ALD) includes wherein the depositing of a layer of zinc oxide ZnO as the surface as the ZnO surface on the SAW sensor includes depositing the layer of zinc oxide ZnO having a thickness of at least 45 nanometers (nm).

25. The SAW biofilm sensor according to claim 19, wherein the method of using atomic layer deposition (ALD) includes the creating of a single atomic layer of aluminum oxide deposition as a passivation layer of the SAW sensor occurring at a deposition cycle rate of 0.09 nanometers per cycle.

26. A surface acoustic wave (SAW) biofilm sensor comprising:
    a first transducer defining an upper surface and a lower surface;
    a second transducer defining an upper surface and a lower surface;
    a piezoelectric film layer defining an upper surface and a lower surface; and
    a passivation film layer defining an upper surface and a lower surface,
    a portion of the lower surface of the piezoelectric film layer disposed on the upper surface of the first transducer,
    another portion of the lower surface of the piezoelectric film layer disposed on the upper surface of the second transducer, and
    the lower surface of the passivation film layer disposed on the upper surface of the piezoelectric film layer,
    the upper surface of the passivation film layer configured thereby to enable contact with a biofilm,
    the SAW biofilm sensor manufactured by a method of using atomic layer deposition (ALD), comprising:
    depositing on a zinc oxide (ZnO) surface of the SAW biofilm sensor in an ALD reactor an aluminum oxide ($Al_2O_3$) film;
    introducing vaporized trimethylaluminum (TMA) $Al_2(CH_3)_3$ into the ALD reactor;
    forming a single layer of the TMA on the ZnO surface;
    purging the single layer of the TMA of unbound TMA vapor to become a purged single layer of the TMA; and
    introducing water vapor into the ALD reactor to create a single atomic layer of aluminum oxide deposition as the passivation film layer of the SAW biofilm sensor.

27. The SAW biofilm sensor according to claim 26, the SAW biofilm sensor further comprising:
    a piezoelectric SAW loss reduction film layer defining an upper surface and a lower surface
    wherein the lower surface of the first transducer is disposed on a portion of the upper surface of the piezoelectric SAW loss reduction film layer and
    wherein the lower surface of the second transducer is disposed on another portion of the upper surface of the piezoelectric SAW loss reduction film layer.

28. The SAW biofilm sensor according to claim 27, further comprising:
    a substrate defining an upper surface and a lower surface,
    wherein the lower surface of the piezoelectric SAW loss reduction film layer is disposed on the upper surface of the substrate.

29. The SAW biofilm sensor according to claim 27, wherein
    a portion of the lower surface of the piezoelectric film layer is disposed on a portion of the upper surface of the piezoelectric SAW loss reduction film layer and disposed between the first transducer and the receiving acoustic wave to electric transducer.

30. The SAW biofilm sensor according to claim 26, wherein another portion of the lower surface of the piezoelectric film layer is disposed between the first transducer and the second transducer.

31. The SAW biofilm sensor according to claim 30, wherein the piezoelectric layer defines an upper sub-layer and a lower sub-layer,
    the lower sub-layer defined by the portion of the lower surface of the piezoelectric film layer disposed on the portion of the upper surface of the lower piezoelectric film layer and disposed between the first transducer and the second transducer,
    the upper sub-layer defined by the portion of the piezoelectric film layer between the passivation film layer and the lower sub-layer,
    the lower sub-layer having a shear modulus and density to define a first SAW velocity,
    the upper sub-layer having a shear modulus and density to define a second SAW velocity wherein the second velocity differs from the first velocity.

32. The SAW biofilm sensor according to claim 30, wherein the piezoelectric film layer defines an upper sub-layer and a lower sub-layer,
    the lower sub-layer defined by the portion of the lower surface of the piezoelectric film layer disposed on the portion of the upper surface of the lower piezoelectric film layer and disposed between the first transducer and the second transducer,
    the upper sub-layer defined by the portion of the piezoelectric film layer between the passivation film layer and the lower sub-layer,
    the lower sub-layer having a shear modulus and density to define a first SAW velocity,
    the upper sub-layer having a shear modulus and density to define a second SAW velocity wherein the second velocity is equal to or greater than the first velocity.

33. The SAW biofilm sensor according to claim 26, wherein the passivation layer includes aluminum oxide, $Al_2O_3$.

34. The SAW biofilm sensor according to claim 33, wherein the passivation film layer defines a thickness between the upper surface of the passivation film layer and the lower surface of the passivation film layer, the thickness of the passivation film layer having a dimension of at least 45 nanometers (nm).

35. The SAW biofilm sensor according to claim 33, wherein the piezoelectric film layer includes zinc oxide, ZnO.

36. The SAW biofilm sensor according to claim 35, wherein the piezoelectric film layer defines a thickness between the upper surface of the piezoelectric film layer and the lower surface of the piezoelectric film layer, the thickness of the piezoelectric film layer having a dimension of at least 40 nanometers (nm).

37. The SAW biofilm sensor according to claim 34, wherein the piezoelectric film layer includes zinc oxide, ZnO.

38. The SAW biofilm sensor according to claim 37,
    wherein the piezoelectric film layer defines a thickness between the upper surface of the piezoelectric film layer and the lower surface of the piezoelectric film layer, the thickness of the piezoelectric film layer having a dimension of at least 40 nanometers (nm).

39. The SAW biofilm sensor according to claim 37,
wherein the first transducer is a transmitting electric to acoustic wave transducer defining the upper surface and the lower surface of the first transducer; and
wherein the second transducer is a receiving acoustic wave to electric transducer defining the upper surface and the lower surface of the second transducer.

\* \* \* \* \*